United States Patent [19]
Gibbs et al.

[11] Patent Number: 5,871,526
[45] Date of Patent: Feb. 16, 1999

[54] PORTABLE TEMPERATURE CONTROL SYSTEM

[76] Inventors: Roselle Gibbs, 221 Twin Lakes Dr., Fredericksburg, Va. 22401; Stuart Horn, 3805 Acosta Rd., Fairfax, Va. 22031; Yale Kadesky, 6116 Beachway Dr., Falls Church, Va. 22041; Buford Walters, 3589 Forestdale Ave., Woodbridge, Va. 22193

[21] Appl. No.: 632,501
[22] PCT Filed: Oct. 13, 1993
[86] PCT No.: PCT/US93/09874
§ 371 Date: Jun. 14, 1996
§ 102(e) Date: Jun. 14, 1996
[87] PCT Pub. No.: WO95/10251
PCT Pub. Date: Apr. 20, 1995

[51] Int. Cl.⁶ ...................................................... A61F 7/02
[52] U.S. Cl. .......................... 607/104; 607/114; 219/527; 165/46
[58] Field of Search ..................................... 607/104, 105, 607/108–112, 114; 219/527–529, 211–212; 126/204; 165/46

[56] References Cited

U.S. PATENT DOCUMENTS

| | | |
|---|---|---|
| 3,548,819 | 12/1970 | Davis et al. . |
| 3,744,555 | 7/1973 | Fletcher et al. . |
| 3,900,035 | 8/1975 | Welch et al. ............................ 607/108 |
| 3,967,627 | 7/1976 | Brown . |
| 4,026,299 | 5/1977 | Sauder .................................... 607/104 |
| 4,335,726 | 6/1982 | Kolstedt . |
| 4,844,072 | 7/1989 | French et al. . |
| 4,846,176 | 7/1989 | Golden . |
| 4,962,761 | 10/1990 | Golden ................................... 607/104 |
| 5,072,875 | 12/1991 | Zacoi . |
| 5,183,039 | 2/1993 | Sarian et al. . |
| 5,201,365 | 4/1993 | Siegel . |
| 5,297,545 | 3/1994 | Infante ............................... 128/204.18 |
| 5,407,421 | 4/1995 | Goldsmith .......................... 607/114 X |
| 5,441,477 | 8/1995 | Hargest .............................. 607/104 X |
| 5,658,324 | 8/1997 | Bailey, Sr. et al. ................. 607/104 X |

*Primary Examiner*—Jeffrey R. Jastrzab
*Assistant Examiner*—Ryan Carter
*Attorney, Agent, or Firm*—Crowell & Moring LLP

[57] ABSTRACT

A light-weight portable temperature control system which includes form fitting disposable therapy pads for selected body parts having serpentine fluid channels therethrough, a programmable microprocessor for controlling the temperature type and length of cycle, quick disconnects for the therapy pad, a thermoelectric cooler with a liquid heat exchanger and a pump for circulating the fluid through the system.

36 Claims, 16 Drawing Sheets

KNEE

ELBOW

ARM

THIGH

SHIN

TORSO

26
HEAD

26
DENTAL

26
EYES

27
SINUS

28
FACE

CHEMO

SHOULDER

HIP

NECK

WRIST

BACK

NECK

WHEEL CHAIR

FINGER

THUMB

TOE

WATER CONNECTION

PORTABLE TEMPERATURE CONTROL SYSTEM

This application is a continuation-in-part of PCT/US92/05332, filed Jun. 26, 1992, and priority thereunder 35 U.S.C. 120 is claimed.

DESCRIPTION

BACKGROUND OF THE INVENTION

1. Field of the Invention

This invention relates to temperature control systems and more particularly to a light weight portable temperature control unit integrating a variety of face and body pads that will conform to the various contours of the face and body to aid in the therapeutic treatment of sports injuries and other forms of trauma, to relieve post operative pain, and to control swelling, bruising and engorgement.

2. Description of Prior Art

After injury and/or surgery, it has been found that controlling the swelling that normally occurs aids in expediting healing. In particular, in the field of cosmetic surgery, the necessity of maintaining a constant temperature, in the range of 34°–40° Fahrenheit, is extremely important to reduce internal bleeding, bruising and swelling.

Localized temperature control of various areas and parts of the human body, after injury and surgery, requires the use of cumbersome heating pads, ice packs, frozen gels, etc. Refrigeration systems which are large and bulky and which possess additional heating elements to raise or control the temperature, have been used to maintain the body, or a portion thereof, have been used to maintain the body, or a portion thereof, at a temperature substantially below the body's normal temperature of 98.6° F.

The use of ice packs, when taken directly from a freezer and not permitted to warm above 32° F., have been found to induce frostbite. Additionally, upon placement on a patient, the ice pack begins to melt and warm up rather quickly, thereby providing a constantly changing temperature at the areas of contact.

Thus, the various cooling techniques presently in use fail to satisfactorily maintain a constant temperature on the desired body areas.

In addition to the requirement of maintaining a constant temperature on the selected areas, there is also a need for a body pad that will comfortably and securely fit the contours of the area being treated as well as a need for providing portability of the heating or cooling unit.

There have been a number of efforts made to meet the described heating and cooling needs.

U.S. Pat. No. 3,074,410 (Foster) discloses an apparatus for temperature control in which a person's skin is heated and cooled by a fluid heat exchange medium. The cooling means comprises a compressor, a heat exchanger, and a by-pass valve for directing the fluid medium either through or past the heat exchanger. A pump runs continuously and the valve shunts the liquid medium around the refrigerating device when cooling of the liquid medium is not required. The apparatus also has a first thermistor adapted to sense the body temperature and a second thermistor to measure the temperature of the pad. The exchange fluid circulates through a pad contacting the patient's body. An electrical bridge means allows for the activation of the cooling and heating means when the patient's temperature is higher or lower than normal. This device has the drawback of being heavy, having high power demands, and allowing only for limited adjustment and programming.

U.S. Pat. No. 3,744,555 (Fletcher) discloses a liquid cooling apparatus possessing an automatic control system. The temperature of the wall of the auditory meatus and four averaged, unweighted skin temperatures are used as input signals to an electro-pneumatic transducer to control a diverter valve in the liquid cooling loop of the liquid cooling garment. The cooling system comprises a circulation pump, a heat exchanger, and a diverter valve connected in a fluid loop. A by-pass line is provided in the loop connecting the inlet side of the heat exchanger with the diverter valve. The diverter valve may be connected to an electro-pneumatic transducer for operation of the diverter valve according to control signals from a controller. The diverter valve is positioned so that the proper proportion of heated and cooled fluid from the discharge side of the heat exchanger is combined for recirculation through a cooling garment. This device does not allow for long term programming of time and temperature, does not have a heating system, and does not allow for a broad range of temperature settings.

U.S. Pat. No. 4,338,944 (Arkans) discloses a therapeutic device comprising a sleeve for covering a portion of a patient's body and having a space to receive liquid, a device for circulating a liquid through the space of the sleeve, and a device for cooling and heating the circulated liquid. The sleeve may have an inflatable external chamber to apply pressure in the sleeve against the patient's body. The device may have an inflation mechanism comprising an air compressor and a pressure regulator in order to inflate the chamber through a conduit.

During operation of the device, the pump circulates the cooling and heating liquid through the conduit, the sleeve space, and a container wherein the liquid is cooled or heated. The cooling and heating system device comprises a plurality of thermoelectric cooling modules, a metallic container having a chamber to retain a liquid such as water or antifreeze, and a variable direct current power supply. The device may have a pair of thermostats which measure the temperature of the liquid in the circulating system.

When direct current is passed through the thermoelectric device, one side or face of the thermoelectric device is cooled while the other side is heated. A reversal of the direction of the current results in a reversal of the sides of the thermoelectric device which are heated and cooled. The direct current of Arkans, however, only allows for the change in voltage to control the temperature of the thermoelectric cooling modules.

U.S. Pat. No. 4,459,468 (Bailey) discloses a fluid circulating system designed for use with a thermal blanket or pad wherein heating and cooling transfer elements are positioned directly in the fluid within the reservoir tank, eliminating the need for condenser structures and the like. More specifically, a temperature transfer means including one or more thermal modules is connected to the tank and electrically interconnected to transfer plates directly exposed to the fluid within the interior of the reservoir tank. A standby switching mode is included to prevent circulation of the fluid through the thermal blanket by a pump structure until the fluid reaches a preselected temperature. A temperature sensor is also in direct exposure to the fluid in the tank and serves to direct the fluid back to a temperature control means. The temperature control means is in turn electrically connected by current regulating and activating means to the thermal modules whereby a continuous path of information flows between the temperature of the fluid being sensed to the temperature control means and back to the thermal modules for activation thereof in order to accomplish the desired temperature.

The temperature control means further includes an adjustable temperature selector to selectively indicate the desired temperature over a wide range such as 40° to 105° F. A meter provides a visual indication of the actual temperature within the tank. The proper current direction through the thermal modules through an automatic hot-cold logic circuit is activated to heat or cool the fluid. Because the transfer plates are in direct exposure to the fluid on the interior of the tank, the cooling device of Bailey is heavy. Additionally, the fluid in the tank takes an appreciable amount of time to either heat or cool.

U.S. Pat. No. 5,097,829 (Quisenberry) discloses a circulating system for automatically cooling or heating a temperature control fluid. The system includes a device for powering the cooling system with pulse width modulated electrical signals, a device coupled to the sensing device for calculating from the sensed temperatures an indication of the temperature of the fluid flowing within the blanket, and a device associated with the powering system for modifying the temperature of the fluid by controlling the pulse width modulation of the power supplied to the thermoelectric cooling device.

The invention includes a fully automatic microprocessor control system for controlling the temperature of a circulated fluid and monitoring the temperature variations over time. The invention also provides for an electronic controller for a temperature control fluid circulation system which is fully programmable and has a display system which allows periodic reprogramming of the system and monitoring of the operating conditions.

The output of the thermoelectric cooling device is controlled by a pulse width modulator for precisely controlling the temperature of the cooling block. The pulse width modulation is coupled to a shift register for controlling the pulse width modulation of the modulator through a bayonet type male connector. Lights indicate the need to add fluid to the system, when the system is ready to begin fluid circulation operation, and when the system is operating properly. The device contains a unitary heat exchange block and thermoelectric cooling devices.

The device also contains a further input provided by a voltage divider to precisely calibrate the inputs to the microprocessor at the factory so that the temperatures sensed at the inputs are very precisely calibrated in the microprocessor.

The temperature of the blanket is determined by a calculation of the mean temperature between the temperature of the fluid at the exit conduit and the temperature of the entrance fluid returning from the patient blanket at the fluid connection. Alternatively, the system may calculate an approximate blanket temperature by adding an experimentally determined set-off value to the temperature of the fluid in a return conduit measured at the sensor near the return conduit's entry into the reservoir.

U.S. Pat. No. 4,108,146 (Golden) discloses a relatively thin bendable thermal pack unit adapted to be molded to conform closely to the contours of a portion of the human body and to retain the molded shape once it has been positioned to circulate a thermal fluid to heat or cool adjacent skin areas to aid in healing and the like. The thermal pack unit of the invention includes a plastic web or sheet having at least one channeled space formed in a surface thereof to form a path for the circulation of the thermal fluid therethrough. The bendable pack unit is formed from two pieces. The first piece is a bendable plastic sheet or web made from a durable plastic material such as polyvinyl which can be easily and readily bent or formed to fit the contour of a predetermined portion of the human body. The bendable plastic sheet has a channeled interior surface having one or more channel spaces or paths formed therein. The channel spaces may be separated by raised pedestal portions or separators to form a network of interconnected channels or paths for circulating the thermal fluid.

U.S. Pat. No. 4,962,761 (Golden) discloses a thermal bandage for heating and cooling which readily conforms to the contours of a body portion to maintain the adjacent skin at a predetermined uniform temperature to aid in heating and the like. The bandage includes a thermal pack mounted to the conformable member with means to either heat or cool the conforming member.

The heat conductive material includes a heat conductive fluid contained within a thin pliable outer material. The outer material is fixed about its perimeter to the thermal pack so that the fluid is in direct contact with it. The thin pliable outer material may also act as a sterile dressing to cover the adjacent skin portion to prevent infection. The conforming material is made of a heat conductive thermoplastic material.

In one embodiment, the pack includes a base, upstanding perimeter walls and a fluid flow changer defined by the base, walls, and conducting surface. The chamber has at least one separator which defines a circuitous flow path through the thermal pack. The conductive surface, which may separate the thermal pack and conforming member, can be constructed of a plurality of separate conducting plates mounted to a thermal pack at the free ends of perimeter walls and separators.

Velcro-type fasteners can be used to attach the pads.

A peltier device may be used which permits both heating and cooling by the use of dissimilar materials and electric current.

SUMMARY OF INVENTION

The present invention effectively overcomes the above noted problems by providing a portable temperature control system comprising a temperature control unit and at least one therapeutic body pad, wherein the temperature control unit comprises:

a means for circulating a temperature control fluid through the temperature control system;

a means for cooling or heating the temperature control liquid;

a liquid heat exchanger coupled to the means for cooling to remove heat from the temperature control liquid;

an electronic programmable temperature controller for minute adjustments of the temperature of the liquid flowing through the system such that the controller can be programmed to provide cooling and heating cycles in any desired sequence for variable periods of time;

a power supply for powering the temperature controller;

a keypad for programming the cooling and heating cycles for variable periods of time, the keypad connected to the electronic programmable temperature controller;

a therapeutic body pad; and means to attach the therapeutic body pads to the temperature control unit.

This invention preferably utilizes an arrangement of the thermoelectric elements to effect a light weight portable cooler. These thermoelectric elements or couplers heat or cool depending on the direction of the current flow through the elements (Peltier effect). The cooler is precisely temperature controlled and can be coupled through quick disconnects to a body conforming pad for effecting the therapeutic result so desired.

The programmable temperature controller includes a microprocessor capable of controlling the temperature of the circulating fluid within ±2° F. of the preset temperature.

The microprocessor of the programmable temperature controller can be programmed to automatically provide heating and cooling cycles in any desired sequence and duration of time.

The power supply of the temperature control unit preferably comprises an international front end power supply having a direct current voltage converter adaptable with an international input power supply functional on either 40 to 60 cycles and 90 to 270 volts AC or operational on battery power. Alternatively, the power supply may be an AC power supply, or the temperature control unit may have more than one power supply.

The therapeutic body pads, which conform to any desired portion of the anatomy of body, comprise:

a noncrimpable flexible structure having fluid passageways defined therein for circulating the temperature controlled liquid therethrough;

input and output coupling means to the fluid passageways, whereby a fluid may be made to flow therethrough;

an outside dermal layer to be placed on a surface of a body part of the patient;

an outside thermal layer; and a fluid conduit layer positioned between the outside dermal layer and the outside thermal layer, wherein said fluid passageways are positioned between the outside dermal layer and the outside thermal layer.

Further features of the invention will become more fully apparent in the following description of the embodiments of this invention and from the appended claims.

DESCRIPTION OF THE PREFERRED EMBODIMENT

Figure 1:
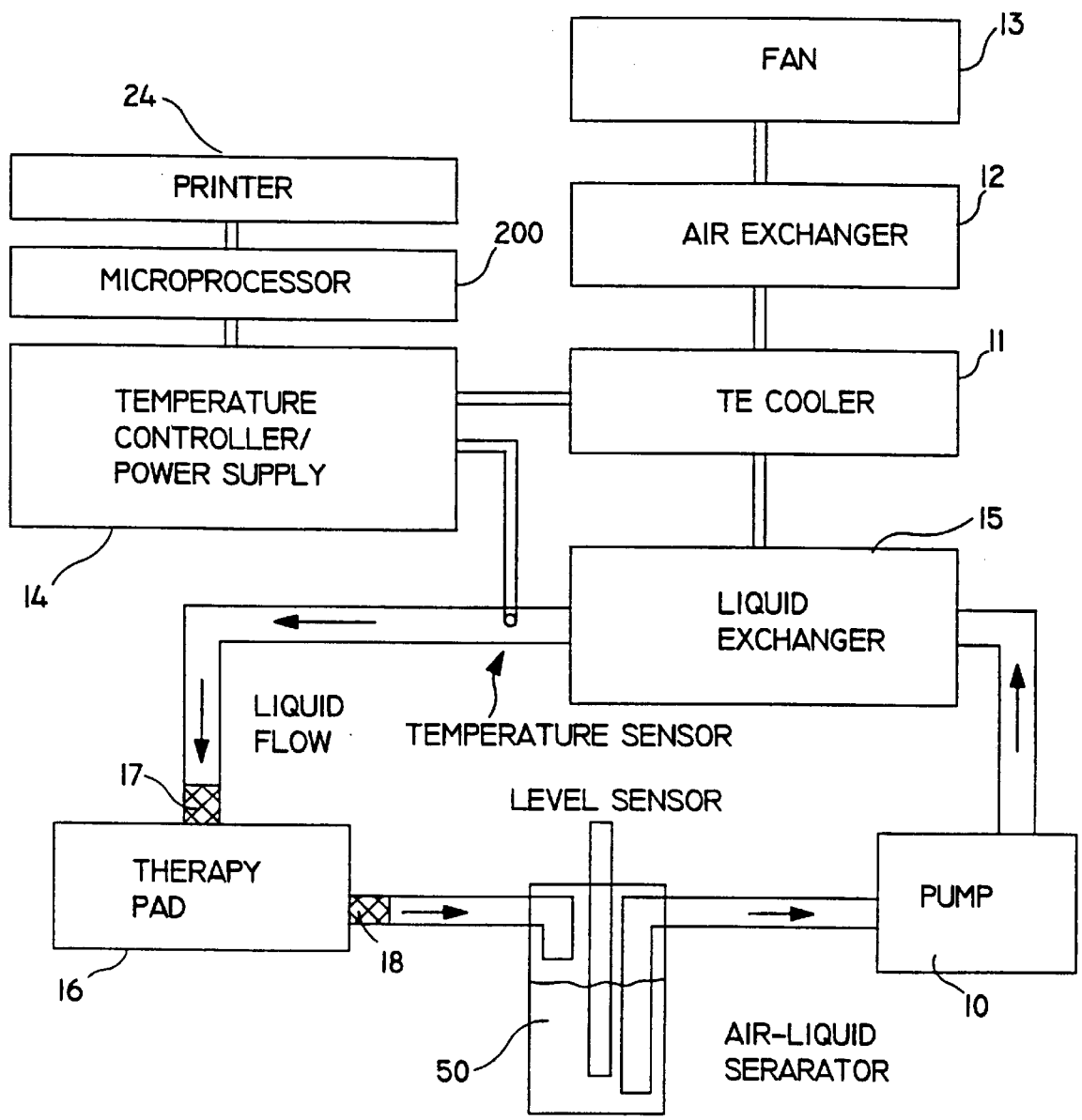
FIG. 1 shows a generalized system block diagram of the present invention.

The generalized block diagram of FIG. 1 shows a temperature control system for controlling the temperature of a body pad as envisioned by this invention, and illustrates the preferable example for packaging the components in a light weight portable system so that they fit into a container the size and general shape of a briefcase or a small piece of luggage. More precisely, the invention relies on computerization, electronic components, and miniaturization of specific parts and components.

The basic components of the portable temperature control system are a means (usually a pump) for circulating the temperature control liquid through the temperature control system, a means for cooling and/or heating the temperature control fluid, a liquid heat exchanger coupled to the means for cooling to remove heat from the temperature control liquid, an electronic programmable temperature controller for minute adjustments of the temperature of the fluid flowing through the system such that the control system can be programmed to provide cooling and heating cycles in any sequence for variable periods of time, a power supply for powering the temperature control system, a keypad connected to the electronic programmable temperature controller for programming the cooling and heating variable periods of time; and at least one therapeutic pad which can be attached by means of tubing to the temperature control unit. The temperature control unit also includes a liquid crystal display screen for communicating with the machine's operator, and liquid electronic displays. The system preferably comprises a dual output system wherein there is a fixed voltage output for the pump and the fan and a programmable voltage for the coolers to regulate the temperature. Alternatively, the power supply may be a single output DC system, and the pump and fan operated from the AC line source.

The temperature control unit serves to cool or heat a temperature control fluid which flows through the unit and the therapeutic body pads. Several fluids may be used as the temperature control fluid, including water, but one of the most desirable fluids has been found to be a mixture of 60 to 90% de-ionized distilled water and 40 to 10% propylene glycol, and most preferably a mixture of 80% deionized water and 20% propylene glycol.

In the preferred embodiment of the invention, each of the elements shown in FIG. 1 such as pump 10, at least one thermoelectric cooler 11, and fan 13, have been improved to function as a DC driven system with a voltage converter which will allow operation of an international input power supply on either 40 to 60 cycles and 90–270 volts AC or as a totally portable unit on battery power.

A thermoelectric (TE) cooler 11 is shown to be the desired cooler in this instance, even though other coolers, such as a split cycle cooler, could be used where portability and weight are not the primary concerns. The thermoelectric cooler is well known in the art and essentially consists of an arrangement of P and N-type semiconductor materials connected electrically for effecting a Peltier effect upon the circulation of current therethrough, and thermally in parallel for effecting a heat sink and a cold sink, in which instance the cooler may be utilized as either a heater or cooler in accordance with the direction of current flow. It is preferred that more than one, and preferably at least six thermoelectric coolers be used in the temperature control unit.

Figure 27:
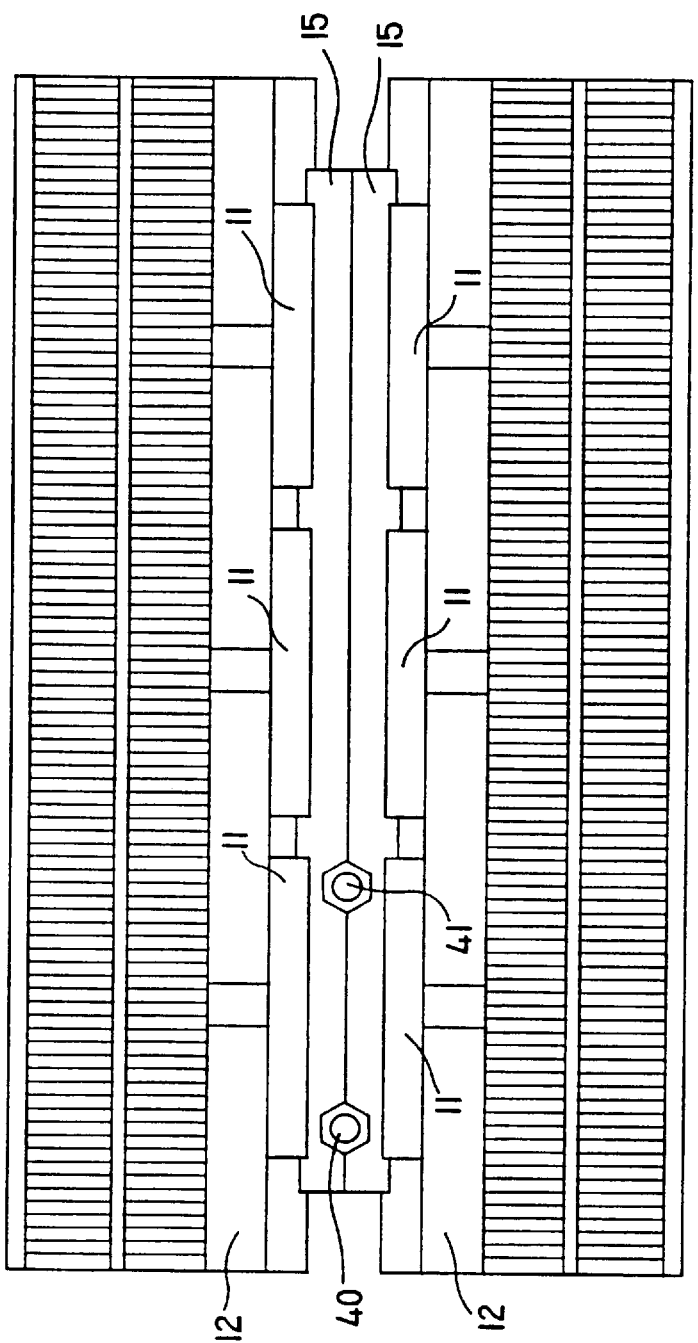
FIG. 27 is an illustration of the cooling system.

As shown in FIG. 27, the thermoelectric cooler(s) 11 is positioned against the liquid heat exchanger to cool (or heat) the temperature control fluid as it is pumped through the liquid inlet 40 and into the heat exchanger 15. The air exchanger 12 is coupled to the thermoelectric cooler 11 such that upon directing the air flow from the fan 13 there across, the heat laden air is removed. The liquid heat exchanger 15 is also coupled to the thermoelectric cooler 11 in such a manner that the liquid flowing through the system and through the liquid outlet 41 is precisely controlled in accordance with the temperature setting of a temperature controller 14 containing a microprocessor 200, which has been refined and made programmable for minute adjustment of the temperature of the liquid flowing through the system to within ±2° F. or better.

The temperature microprocessor controller also can automatically provide a cooling and heating cycle useful in treating sports injuries, for treatment of multiple sclerosis, rheumatoid arthritis or other ailments. For example, the controller can be programmed via the microprocessor, for example, to provide desired periods of cooling and heating.

The microprocessor 200 is integrated into the temperature controller 14 and may be operated manually or in an automatic mode. In the manual mode, the user may set the desired fluid temperature. This regulates the power supply to control the current flow through the thermoelectric cooler 11 of FIG. 1 and is automatically adjusted to meet the temperature setting. In the automatic mode, the user merely sets a temperature cycle to be observed. For example, the user can have the temperature set at a low (cool) setting for a predetermined period of time followed by a higher (warm) temperature setting for another predetermined period. This cycling can continue and be repeated indefinitely.

Thus, the microprocessor of the programmable temperature controller can be programmed to automatically provide heating and cooling cycles in any desired sequence and duration of time.

The microprocessor also allows for the presetting of a prescripted heating and cooling therapy, which can only be utilized by the use of a prescription passcode. That way a physician can punch in his prescription passcode, unknown to the patient, program the heating and cooling therapy he desires for the patient, and then electronically lock those settings into the temperature control unit so that the patient can not alter the temperature and time settings.

The microprocessor adjusts the temperature of the temperature control fluid to the preset required parameters by determining the amount of adjustment needed from skin temperature sensors, located on the therapeutic body pads, and/or a temperature sensor located in the heat exchange unit, the amount of adjustment needed. For example, if the temperature control unit has been preset at 40° F. to be determined by the temperature of the skin, and the skin temperature sensor communicates to the microprocessor that the temperature of the skin is 43° F., the microprocessor will send a signal to increase the voltage of the thermoelectric coolers to reduce the temperature of the temperature control fluid by a certain amount. The temperature sensor located in the heat exchange unit will send signals to the microprocessor to indicate any change in temperature of the temperature control fluid. The skin sensor will continue to send signals indicating the skin temperature, such that when the skin temperature is reduced to 40° F., the microprocessor will continuously signal the thermoelectric cooler to increase or decrease the cooling effect accordingly to maintain the skin's temperature at 40° F.

The microprocessor is set by the use of a keypad. Temperature adjustments and readings may be determined by the use of a skin temperature sensor or a control fluid temperature sensor positioned in or at the liquid heat exchanger, and connected to temperature controller 14. The settings, temperature, directions and feedback are visualized on a liquid crystal display screen, also connected to and part of the temperature controller. Communication of the unit with the operator is also assisted by LEDs, which are also part of and connected to the temperature controller 14.

Figure 13:
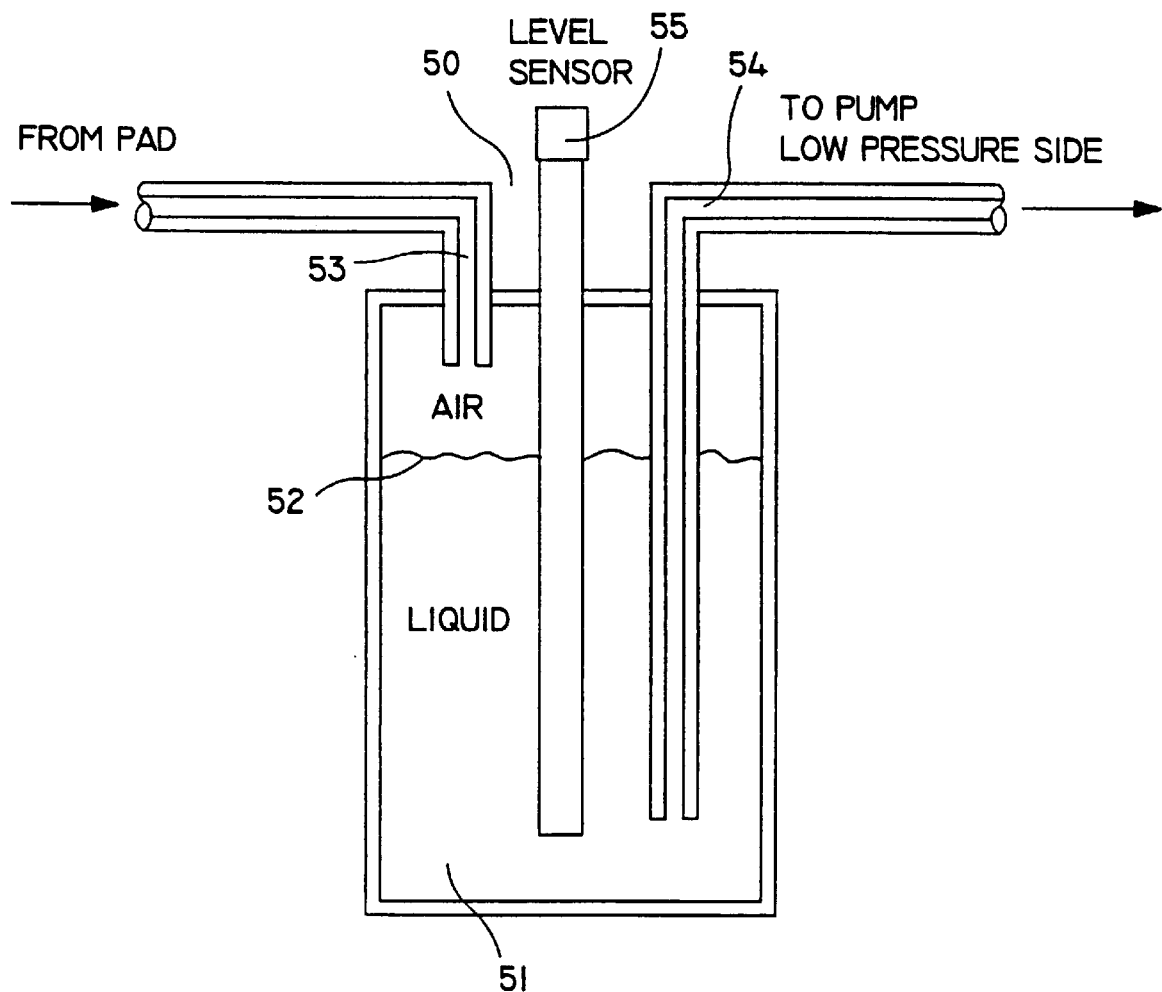
FIG. 13 is a cross-sectional view of the air liquid separator.

As shown in FIGS. 1 and 13, the temperature control unit also comprises an air liquid separator 50 in the temperature control unit for separating air from the temperature control fluid as the temperature control fluid is recirculated through the pads and the portable temperature control unit prior to the temperature control fluid entering the pump and after exiting the therapeutic pad. The air liquid separator 50 comprises a small reservoir 51 for containing the temperature control fluid 52, a shortened tube 53 for transporting the temperature control fluid from the body pad to the reservoir, and an exit tube 54 extending from near the bottom of the reservoir and leading to a low pressure side of the pump. The shortened tube empties the temperature control fluid above the highest level of the fluid in the reservoir. This way, any air in the temperature control fluid separates from the fluid in the air-liquid separator.

The temperature control unit also has an audio alarm system mounted to the front panel to indicate restricted flow of the temperature control fluid, low levels of the temperature control fluid by sensor 55 in the air liquid separator, malfunctions of the temperature settings when the system is powered on, when a cycle is completed or when an error exists. The visual liquid crystal display screen indicates the nature of the problem when the alarm system sounds.

Figure 14:
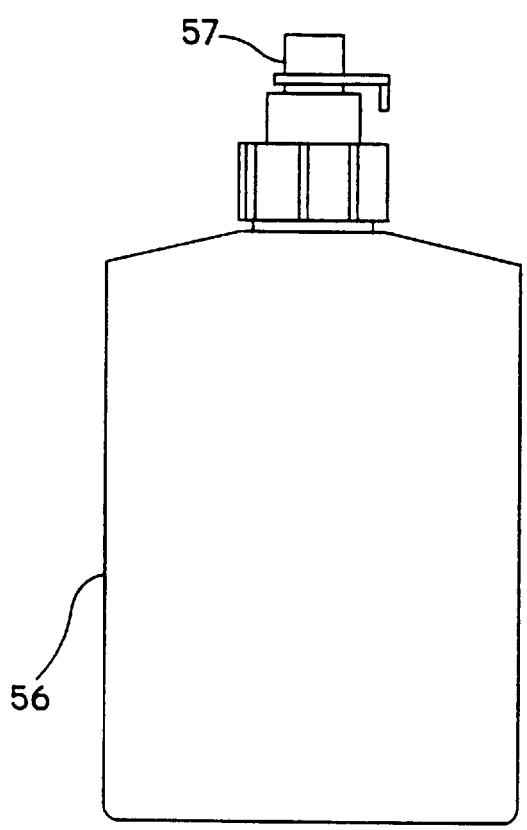
FIG. 14 is a frontal view of the fill bottle.

If the fluid level of the air-liquid separator does drop too low, then the temperature control system may preferably be recharged by means of squeezable fill bottle 56 of FIG. 14. The fill bottle has a quick disconnect 57, preferably with a male outlet to refill the temperature control fluid in the air-fluid separator.

Figure 15:
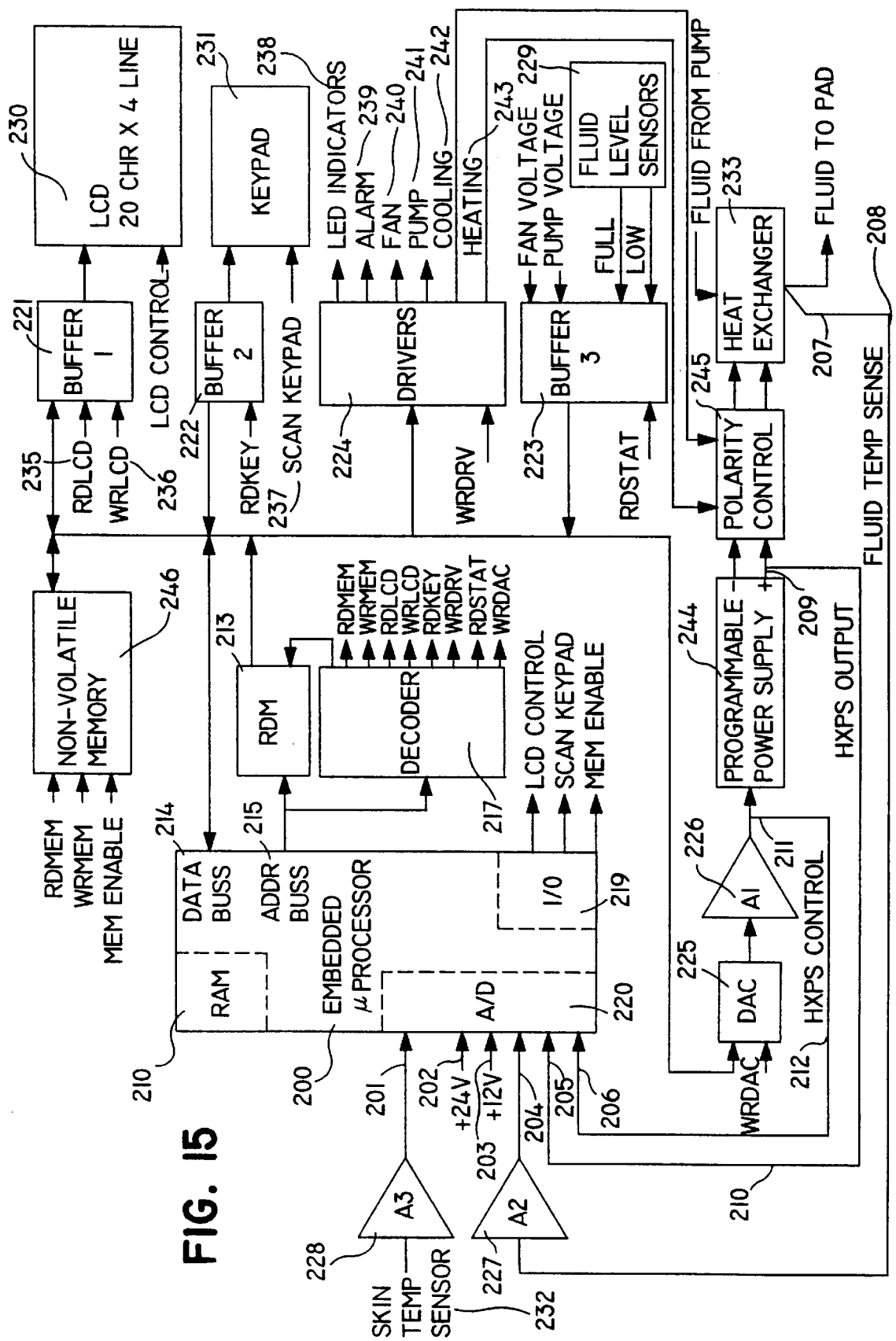
FIG. 15 is a block diagram of the electronic systems of the temperature control unit.

Referring to FIG. 15 a block diagram of the control circuitry for the system of the present invention illustrates the electronic relationships of the various components of the system. The microprocessor 200 has an internal RAM 210, I/O (Input/output) 219 and A/D (Analog to Digital) 220 and external ROM 213, DECODER 217, NON-VOLATILE MEMORY 246, BUFFERS 221, DRIVERS 224, DAC (DIGITAL TO ANALOG CONVERTER 225), with AMPLIFIER (AI) 226, TEMPERATURE SENSE Signal Conditioning Amplifier (A2 227, A3 228), FLUID LEVEL SENSORS 229, LCD DISPLAY 230, and KEYPAD 231.

The microprocessor receives its instructions from the stored program located in the ROM 213 via the connected DATA BUSS 214. The microprocessor also sends and receives data to and from the several BUFFERS 221, 222, 223, DRIVERS 224, NON-VOLATILE MEMORY 246, and the DAC 225 via the connected DATA BUSS 214. Using address information derived from the ADDRESS BUSS 215, the DECODER 217 determines which of the devices connected to the DATA BUSS 214 are to be written to or read from.

The NON-VOLATILE MEMORY 246 is used to store current system setup/status data (4) user programmable setups, and ongoing history data for evaluation.

Analog inputs 201 to 206 to the A/D section 220 of the microprocessor 200 are from a plurality of sensing devices.

The microprocessor 200 may be of different types, although the Intel 801C196KB is preferred. A/D input 201 comes from signal conditioning amplifier A3 228 which conditions the signal from the skin temperature sensor 232. A/D input 204 comes from signal conditioning amplifier A2 227 which conditions the signal via line 208 from the fluid temperature sensor 207 which is mounted on the heat exchanger 233. A/D input 205 comes from the output of the programmable power supply 244 via line 209 while input 206 comes from the output of the DAC amplifier A1 226 via line 212 to provide the means of monitoring all elements of the control path for correct operation. A/D input 202 is connected to +24V and A/D input 203 is connected to +12V which are the system power supplies and provides the means for the microprocessor 200 to monitor the system power supplies.

Messages are displayed by writing/reading LCD 235, 236 via BUFFER 1 221 to the LCD 230. Keypad closures are detected by Scanning 237 the KEYPAD 231 and reading via BUFFER 222. LED INDICATORS 238 are operated by writing to appropriate DRIVERS 224. LEDs are provided to show selected function (SINGLE CYCLE, MULTIPLE CYCLE, MEMORY, OPTIONS, PRESET), START, STOP, LOW TEMP CYCLE, HIGH TEMP CYCLE, LOW FLUID, and SYSTEM FAILURE. Additionally, DRIVERS 224 are provided to operate the ALARM 239, FAN 240, PUMP 241, COOLING control 242 and HEATING control 243. The COOLING control 242 and HEATING control 243 outputs in turn operate the POLARITY control 245.

The DAC output 225 is passed through AMPLIFIER (A1) 226 and then to the PROGRAMMABLE POWER SUPPLY 244 which in turn powers the HEAT EXCHANGER 233. In this context, the PROGRAMMABLE POWER SUPPLY 244 is regarded as a power amplifier which will apply a variable DC voltage as required by the controller, to the HEAT EXCHANGER 233. This provides a precise means to control the amount of cooling/heating generated by the HEAT EXCHANGER 233.

Upon initiation of a cooling/heating cycle, the system will set the POLARITY CONTROL 245 for cooling/heating as required and begin to monitor the fluid temperature via the FLUID TEMPERATURE SENSOR 207. The system applies power to the HEAT EXCHANGER 233 via the PROGRAMMABLE POWER SUPPLY 244 as required by the controller to maintain the preset FLUID TEMPERATURE 207. If the optional SKIN TEMPERATURE SENSOR 232 is used, the system still uses the FLUID TEMPERATURE SENSOR 207 as the primary control element. However, the system will modify the fluid temperature in order to attain the preset skin temperature. This ensures that even if the skin temperature probe is improperly placed, the system will still have the ability to maintain the fluid at a temperature that will not damage skin.

Additionally, the system continuously measures the output of A1 (HXPS CONTROL) 226 and the output of the PROGRAMMABLE POWER SUPPLY (HXPS OUTPUT) 209 to insure that the control voltage and power output are being correctly generated. If either of these two conditions fail to match the expected response, this will be considered a "fault" condition and the system will terminate the current temperature cycle and display a message on the LCD 230 indicating to the user which fault condition has occurred.

Additionally, the system measures the +24V (PRIMARY SYSTEM POWER SUPPLY) 202 and +12V (ANALOG POWER SUPPLY) 203, monitors presence of FAN and PUMP voltages, and the LOW FLUID sensor for "fault" conditions. As above, the system will terminate the current temperature cycle for any "fault" condition.

As this system does not use pulse width modulated power which radiates high energy switching into the environment or substantial power which would interfere with other medical equipment in the environment or even the controller itself, the unit may be used in hospital rooms, and the PROGRAMMABLE POWER SUPPLY 244 has been approved for hospital use per UL 544. While the system may contain a "brushed" motor, the unit preferably contains a brushless DC (or AC) motor which would further reduce any possible interference with other medical or other electronic equipment.

Another optional feature for this temperature control unit is a printer 24 either external to the unit or internal. More specifically, the microprocessor sends a signal to a printer 24 which is either connected within the housing of the temperature control unit or which may be connected to the temperature control unit by means of a jack. For example, the pressing of a print function key on the keypad or the punching in of a code may signal the temperature control unit to print out on the printer either the cycles and temperatures at which the temperature control unit has been operating or the cycles and temperatures for which the temperature control unit has been programmed.

An extremely important feature of this invention is the noncrimpable flexible therapy pad 16. Pad 16 is connected in the system with two sets of quick disconnects, one shown as 17, being coupled to the liquid heat exchanger 15 and the other being 18, which is coupled to the pump 10, for return of the fluid. The quick disconnects allow a pad, which is precharged with liquid, to be quickly connected and disconnected to the portable cooling machine. The quick disconnects may be connected to side loading tubes to avoid crimping of the fluid line. Even though the temperature control unit cooler as shown in FIG. 1 shows a single therapy pad 16, the design allows for multiple ports for treating several body parts simultaneously and even at different temperatures.

Figure 2:
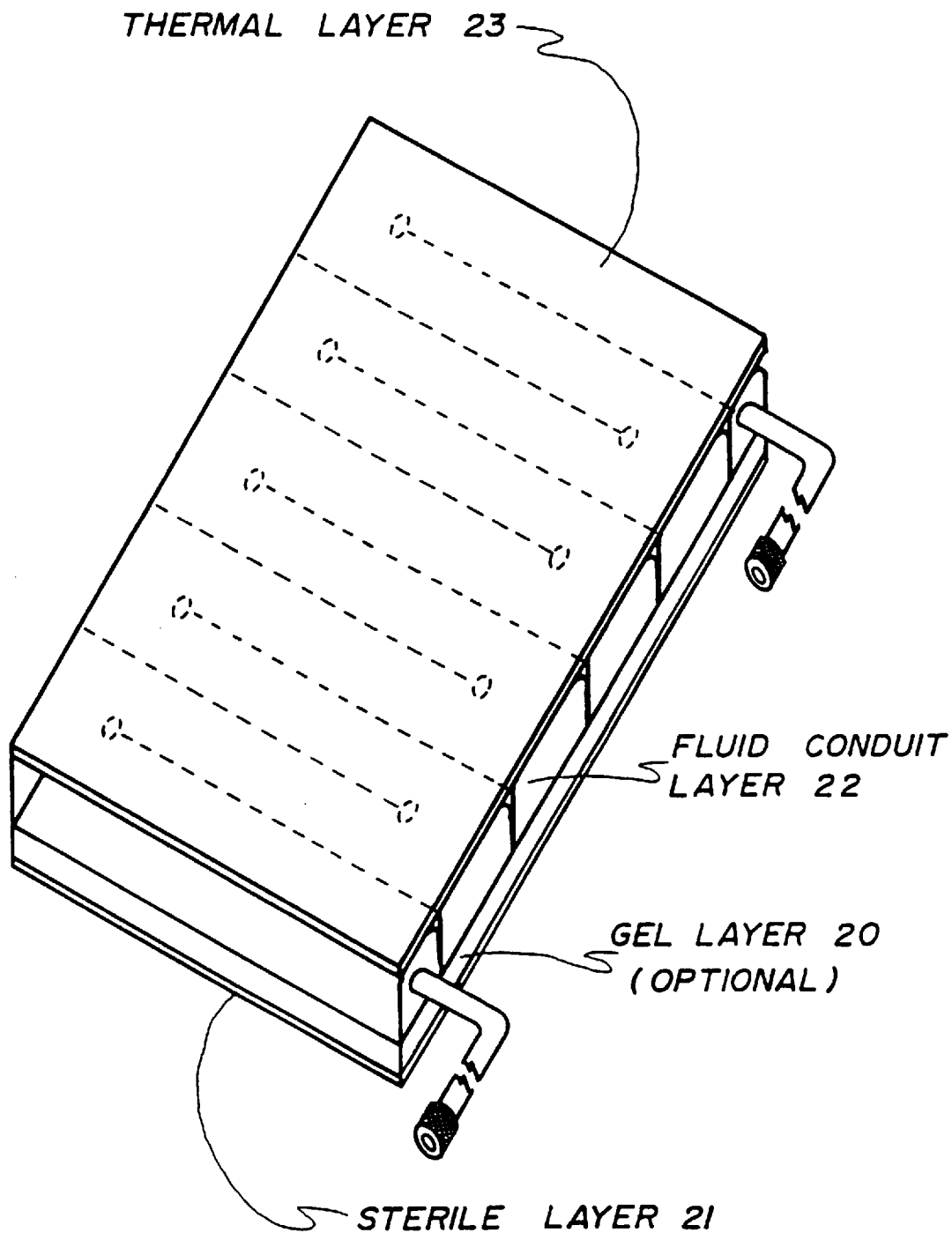
FIG. 2 shows one embodiment of a body conforming pad of the present invention.
Figure 25:
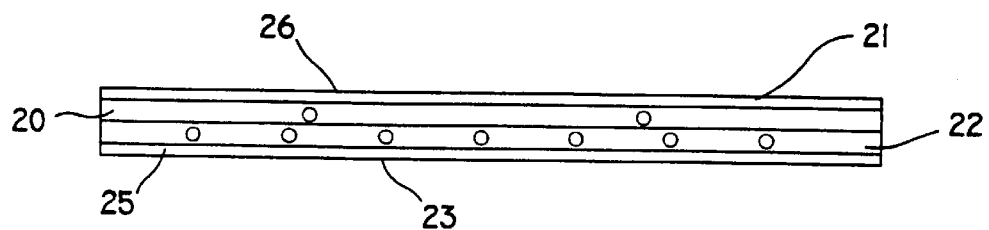
FIG. 25 is a cross-sectional view of a pad.

However, one of the major advantages of this system lies in the body conforming pad generally shown in FIGS. 2 and 25. The gel layer 20 actually represents an alternative embodiment of this invention and is sandwiched between a sterile pad shown as layer 21 contacting the body and a layer of fluid carrying conduits shown as layer 22 composed of flexible serpentine fluid conduit passageways, more clearly shown in FIG. 3b. The gel 20 is a soft readily movable material having a good temperature conducting characteristic such that the entire cooled or heated area maintains an even temperature gradient and as such, maintains a more constant temperature at the point of treatment. The gel layer preferably is filled with polyglycol and barium or magnesium ions, or with silicon, and is preferably between 1/16" to 3/8" thick, and more preferably between 1/8" to 1/4" thick. The fluid layer is preferably between 1/16" to 1/2" thick and more preferably between 1/4" to 3/8" thick.

A thermal layer 23 insulates the pad from the outside environment in order to maintain a constant temperature at the point of contact with the body. This layer 23 may take various forms but in the preferred embodiment it is envisioned as one or more layers of material, such as polyurethane, of a thickness of approximately 0.008 mil, having an air pocket 25 to provide flexibility and good insulative qualities or a thin insulating material in the air space. The body pad may take the form of the area being treated and may be of any reasonable size from that of a small pad to a large portion of the body. The thermal layer may have a thickness of between 1/16" to 1/8".

Layer 21 of the pad, which may be referred to as the dermal layer 26 as this layer faces the skin, may be fabricated as a sterile disposable pad, such as polyurethane, or as a removable and reusable pad or layer which is durable and capable of being sterilized repeatedly. This layer 21 may be affixed to the cooling pad by various techniques, one being by use of Velcro strips to allow for ease of replacement. It should be recognized that the pad shown in FIG. 2 is by way of representation only and may be fabricated of multiple layers to meet the particularly need. Alternatively, layer 21 may not be the sterile layer, but may instead be a layer which allows for the attachment of a sterile layer or material such as a paper or plastic gauze. Means of attachment of the layer may include a hook and loop fastener system such as VELCRO strips on layer 21 and/or on the sterile layer. Specifically designed body pads, such as face masks, and other body conforming designs are envisioned as applications of this invention. The dermal layer is preferably no greater than ⅛" thick, and a detachable sterile pad or layer may be as thin as a sterile paper or cloth tissue.

Figure 3A:
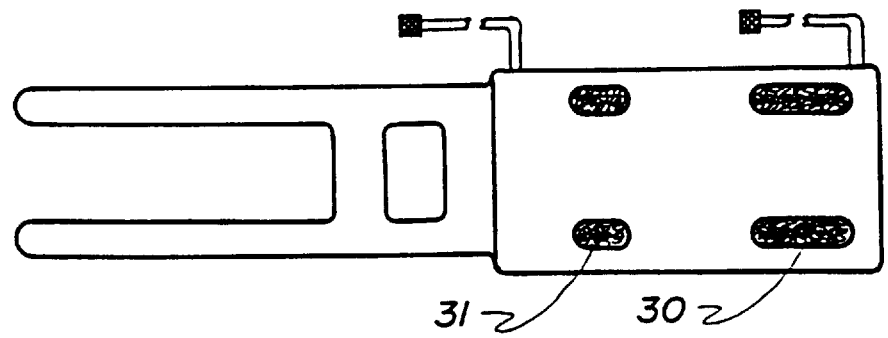
FIGS. 3a, 3b and 3c show the various views of a detailed arrangement of the serpentine fluid jacket of FIG. 2.
Figure 3B:
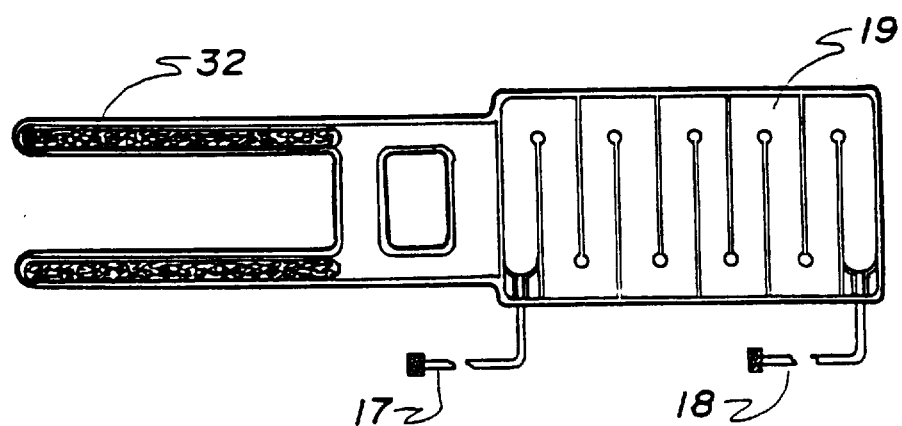

Looking more specifically at FIG. 3b, quick disconnects 17 and 18 allow ease of coupling and decoupling of the pad, without the loss of system fluids. The fluid flow lines are designed such that the pad bends around the body contour with the flow lines parallel to the pad bend. The flow lines are preferably fabricated of a polyurethane material. This enables the pressurized fluid within the lines to conform to the body part without crimping fluid flow.

Figure 3C:
Figure 4A:
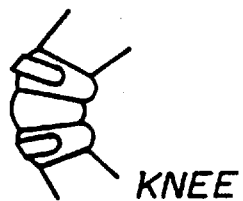
FIGS. 4–12 show various designs of the body, head and face pads.
Figure 4B:
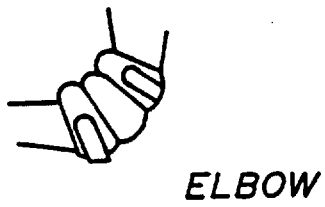
Figure 4C:
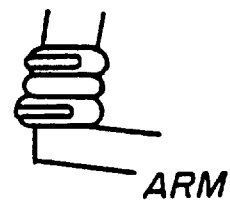
Figure 4D:
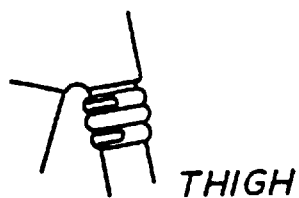
Figure 4E:
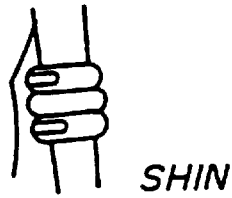
Figure 4F:
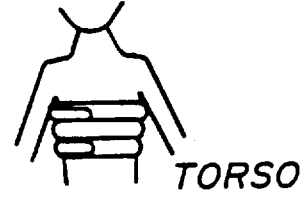

Even though the fluid passageways 19 of the pad in FIG. 3b are shown in a parallel configuration, they are actually configured in each specifically designed pad to bend and flex with the contour of the body part to which the pad is to conform. This design is necessary to assure that the fluid flow through the passageways is not restricted or pinched off. The cutaway side view of the pad in FIG. 3C, further shows the extremely high percentage of surface area of the pad functioning as a fluid flow and temperature control area. Referring to FIG. 3a, strips 30 and 31 are shown as a hook and loop fastener such as VELCRO strips whereby the pad may be securely attached to a body part being treated by fastening the strap, also having a VELCRO strip 32 shown in FIG. 3b, around the body part to mate the respective VELCRO strips 30 and 31 to the strip 32.

Various types of pads are shown in FIGS. 4 through 12. The pads are designed for specific areas of the body and are shown for illustrative purposes only. They do not show the required quick disconnects or specific attachment means as exemplified in the basic design of FIGS. 3a, 3b and 3c. In FIGS. 4a, b, c, d, e, and f, a universal pad is shown adapted to the knee, elbow, arm, thigh, shin and torso, respectively.

Figure 5A:
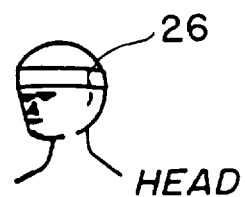
Figure 5B:
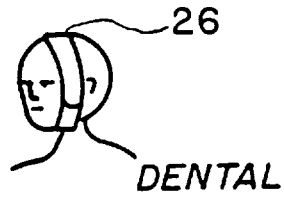
Figure 5C:
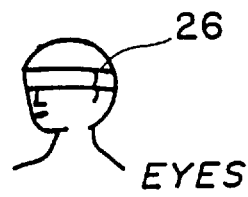
Figure 6A:
Figure 6B:
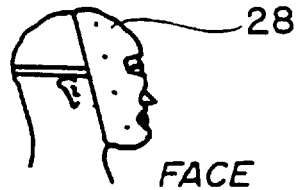
Figure 17:
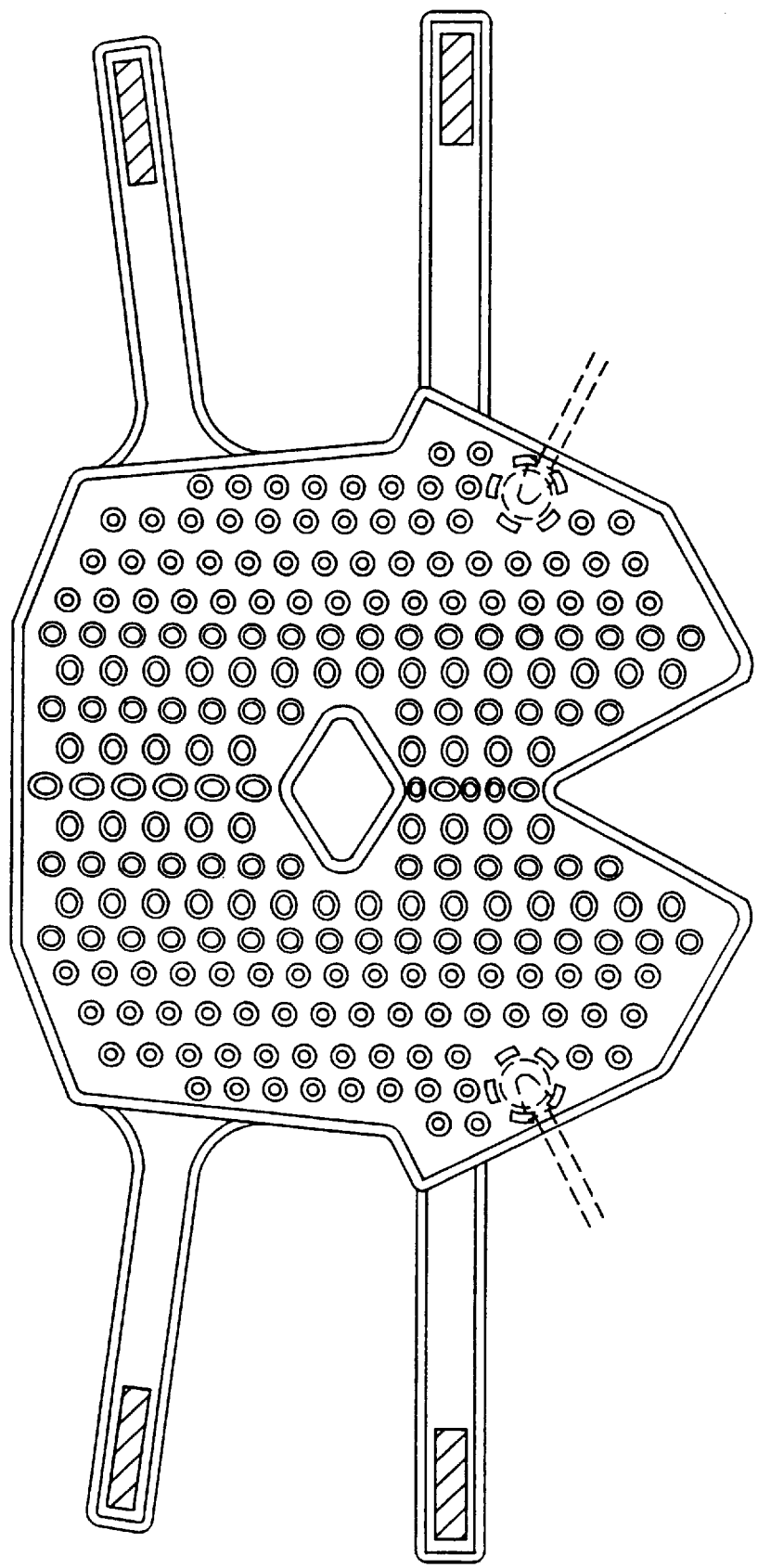
FIG. 17 is an illustration of a face mask pad.
Figure 18:
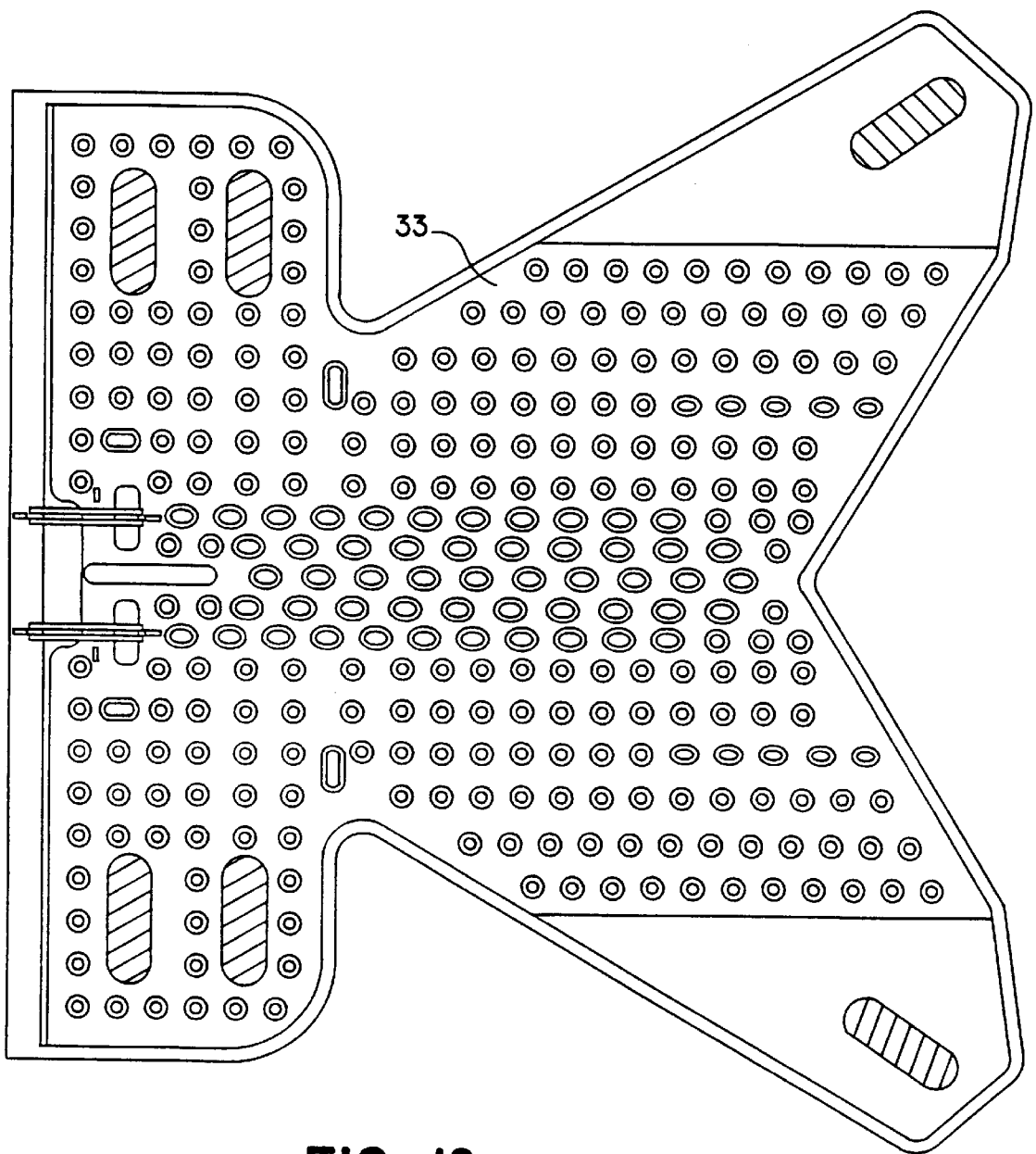
FIG. 18 is an illustration of a hip and shoulder pad.
Figure 23:
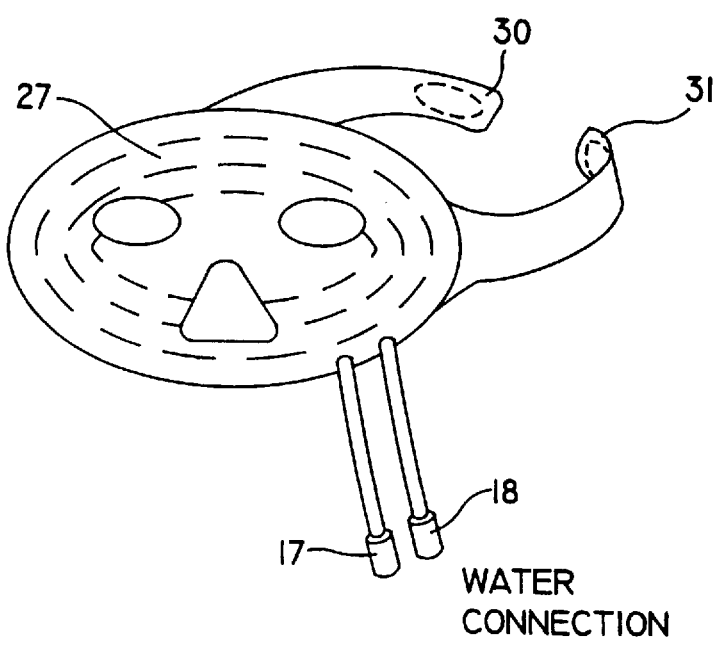
FIG. 23 is an illustration of a sinus mask.

FIGS. 5a, b and c, illustrate the application of the pad as headband 26, FIGS. 6a and 23 show a sinus face mask 27 and FIG. 6b shows a face mask 28 which is configured to conform to ones face for cosmetic surgery or facial injury recuperation. The mask may be held securely in place by adjustable or VELCRO straps 30, 31 attached thereto for coupling in a comfortable arrangement around the head. FIG. 17 shows a face mask pad which is attached to the face by means of long strips with velcro attachments 30, 31 at the end, which are attached at the back of the patient's head. An opening in the center of the face mask allows the patient nostrils to protrude. The gel layer of the face masks 27 and 28, headband 26, and other pads which conform to various body parts may have welded sections which form pockets to so that the gel in the gel layers will not migrate.

Figure 8A:
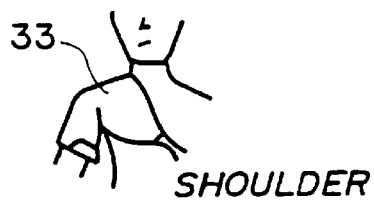
Figure 8B:
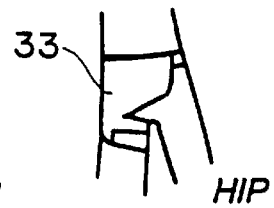
Figure 9:
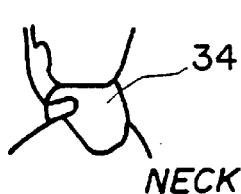
Figure 10:
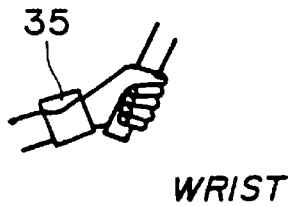

FIGS. 8a and b and 18 show shoulder and hip pads 33 which is designed to be wrapped around either of the two body parts, while FIG. 9 shows a collar or neck pad 34 and FIG. 10 shows the use of a wrist band pad 35 for carpal tunnel, fatigue and sports injuries.

Figure 11A:
Figure 11B:
Figure 11C:
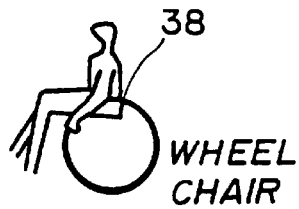
Figure 12A:
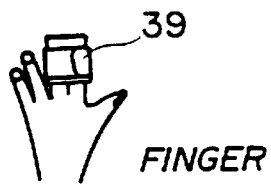
Figure 12B:
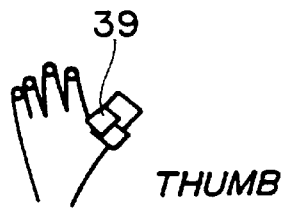
Figure 12C:
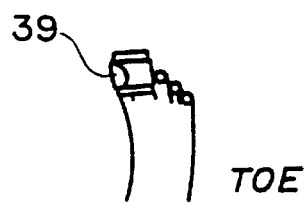

FIGS. 11a, b, and c show back 36, neck 37 and seat 38 pads while FIGS. 12a, b, and c show applications of the appropriate shaped pads 39 to the finger, thumb and toe.

Figure 7:
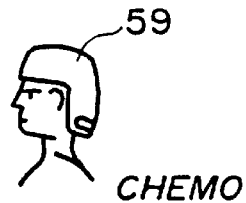
Figure 16:
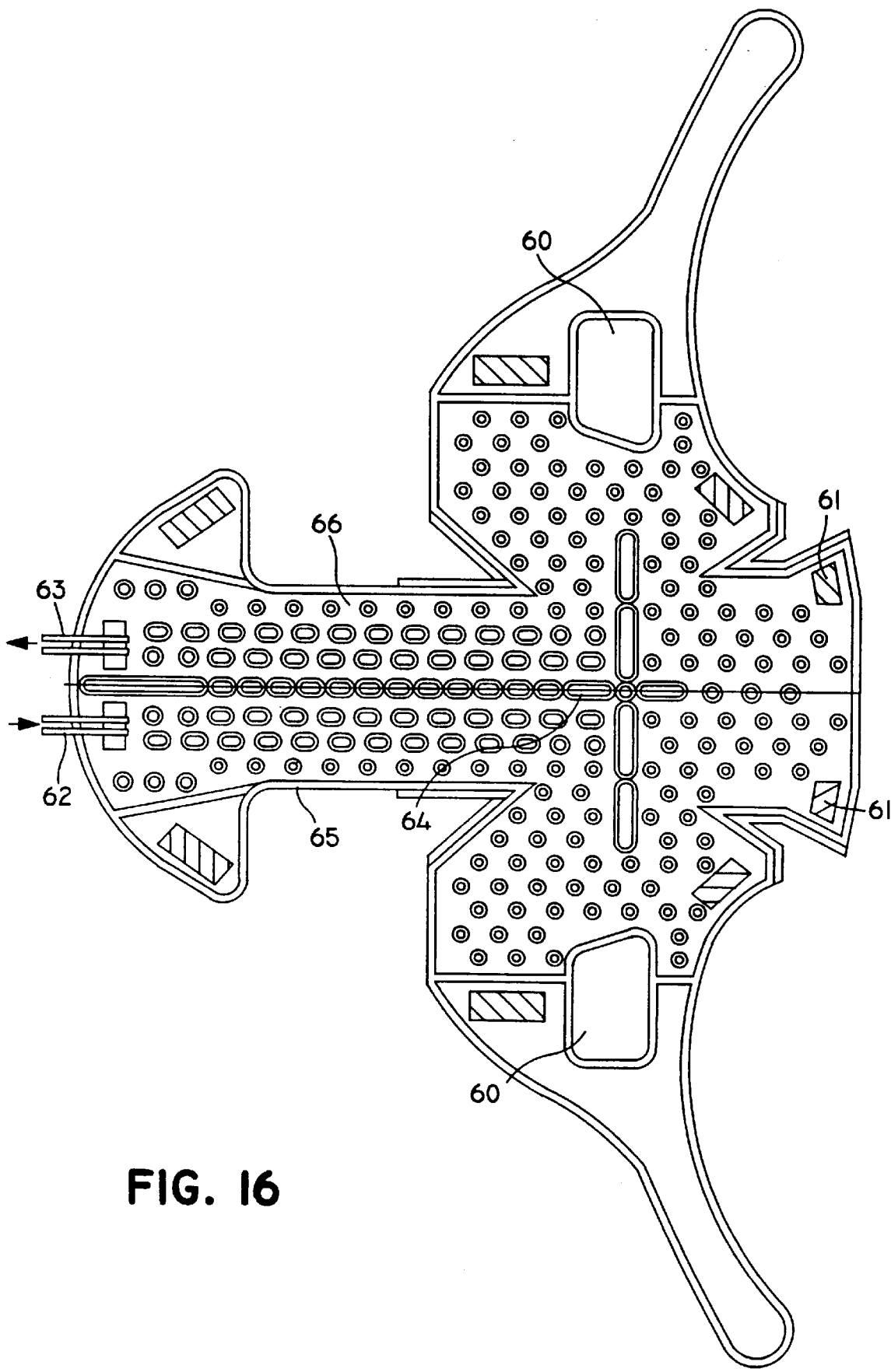
FIG. 16 is an illustration of a cryo-cap.

FIGS. 7 and 16 show a cryo-cap body pad 59. This cap 59 is particularly useful for cooling scalp treatments during cancer chemotherapy, to prevent or reduce hair loss which normally occurs as a result of such treatments. The inside of the cryo-cap may be lined with felt (not shown) which can be wetted to allow for improved thermal conductivity. It should be noted that any of the body pads can be lined with felt for the same purpose. Alternatively, the cryo-cap may have a gel layer.

Additionally, the cryo-cap has openings 60 allowing the patient's ears to protrude from underneath the cap. Additionally, the cryo-cap has velcro strips to secure the cap to the patient's head, and has, of course, a temperature control fluid inlet 62 and a temperature control fluid outlet 63, which may be quick disconnects. The cryo-cap also preferably has an intersecting walled structure 64 to separate the input 62 and output coupling 63 means to prevent the temperature control fluid flowing into the liquid passageways through the input coupling from flowing directly out of the output couplings. Other therapeutic body pads may also preferably contain this feature. Depending on the size and design of the body pads, there may also be spacings or openings positioned in the intersecting walls to allow for flowthrough of the fluid.

Additionally, the fluid passageways along the outer borders of the body pad 65 are preferably wider than the fluid passageways 66 away from the outer borders of the body pad so that the temperature control fluid is evenly distributed as it flows through the body pad. This flow arrangement is applicable to any of the therapeutic body pads described herein.

The cryo-cap also has a hook and loop fastener system such as VELCRO strips 61 for ease of attachment and securing.

Figure 19:
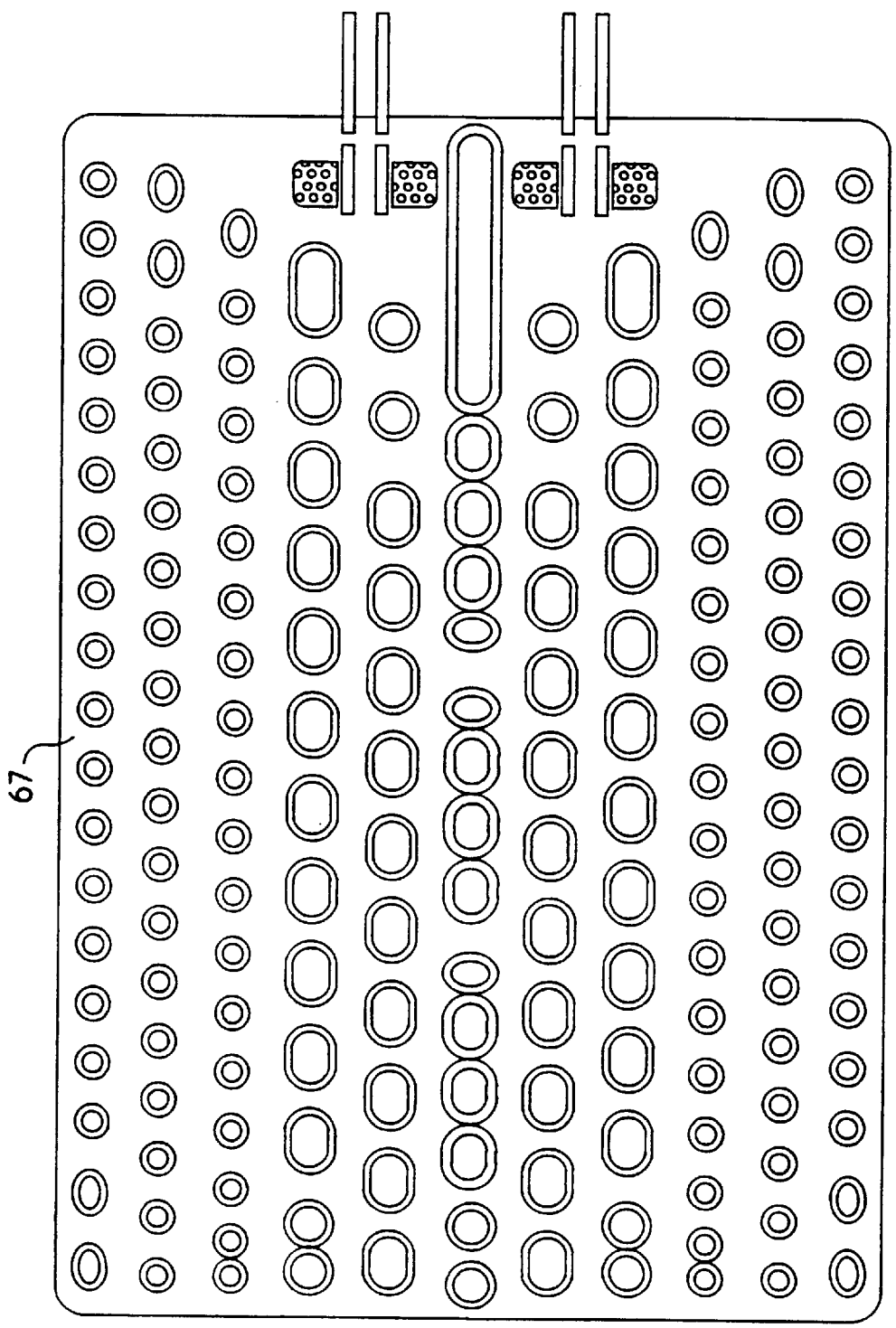
FIG. 19 is an illustration of a large universal pad.
Figure 24:
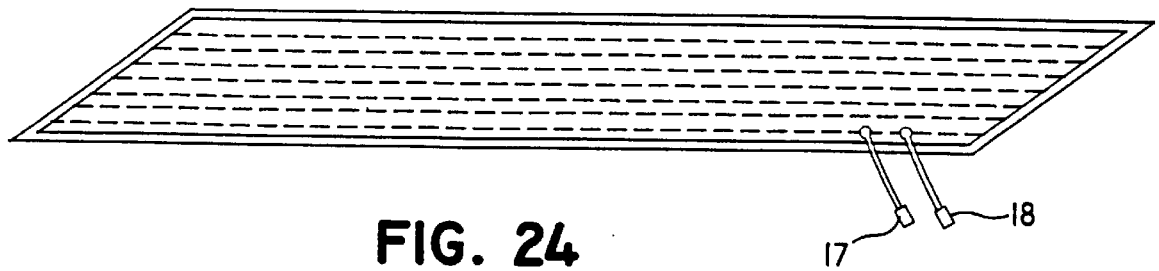
FIG. 24 is an illustration of a blanket pad.

FIG. 19 is an all purpose large universal pad 67, and FIG. 24 is a blanket pad 75 helpful in treating back ailments.

Figure 20:
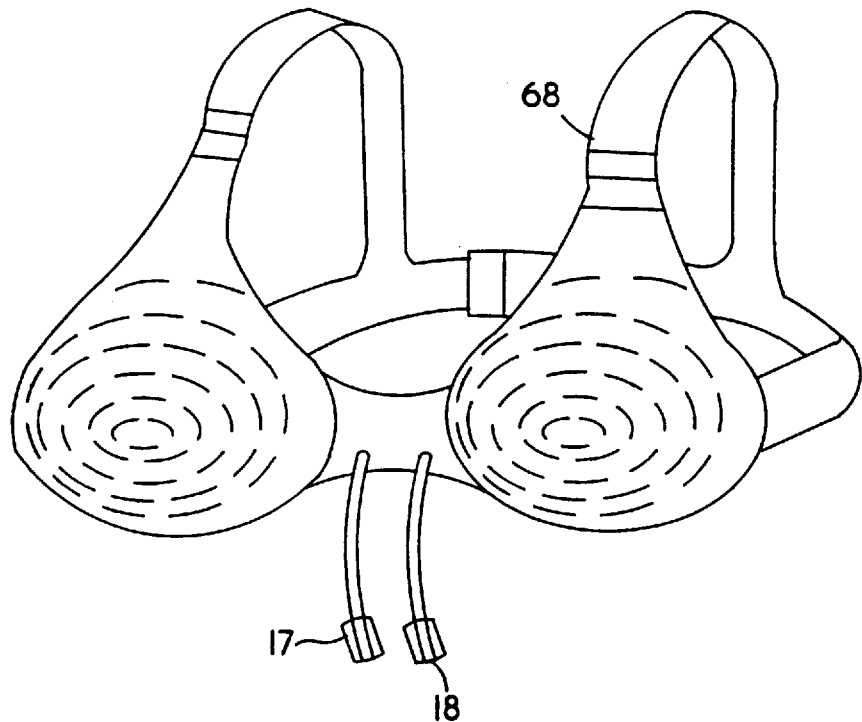
FIG. 20 is an illustration of a brassiere pad.

FIG. 20 is a brassiere pad 68, which is particularly useful for use after breast reduction or augmentation surgery, lumpectomies, or during or just after the nursing cycle. The brassiere pad may come in different sizes with adjustable straps.

Figure 21A:
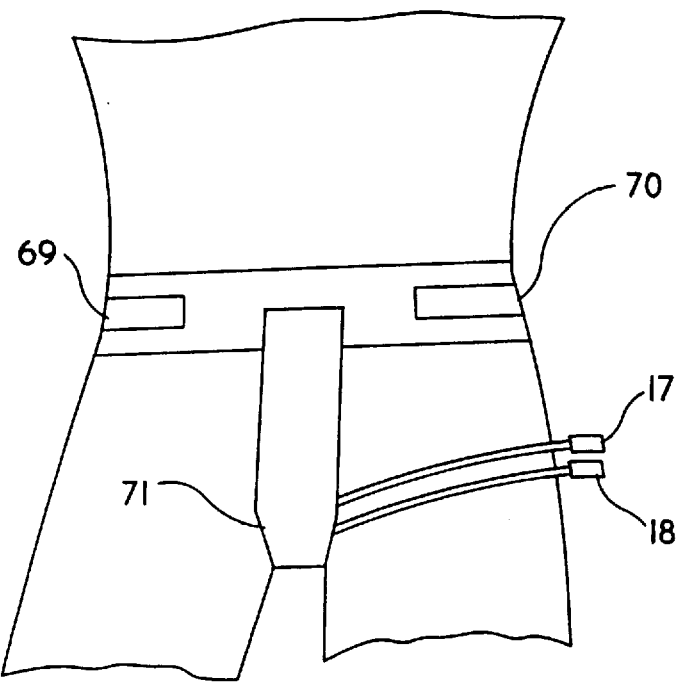
FIGS. 21A–B are illustrations of an orificial pad.
Figure 21B:
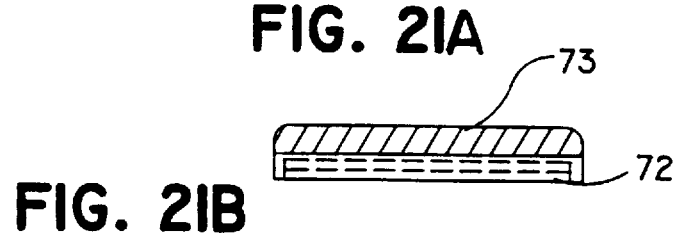

FIG. 21A shows an orificial pad 69. It is designed be used as a vaginal insert pad after surgery or after a woman has given birth. Alternatively, it can be used as an anal insert pad for use after surgery, and particularly after hemorrhoidal surgery. The pad contains a support belt 70 with velcro strips, fluid input and output connections 17, 18 and the orificial insert 71 itself with a cold layer 72 and an adsorbent cover 73 surrounding the cold layer 72 (see FIG. 21B).

Figure 22:
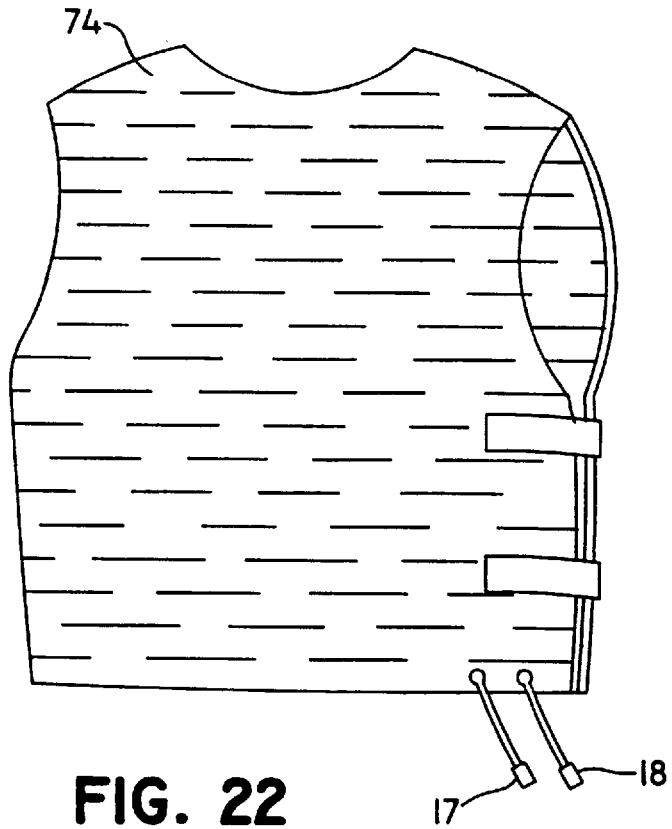
FIG. 22 is an illustration of a vest pad.

FIG. 22 shows a therapeutic vest pad 74. It may be used to treat hypothermia, hyperthermia, or to treat swollen muscles.

Figure 26:
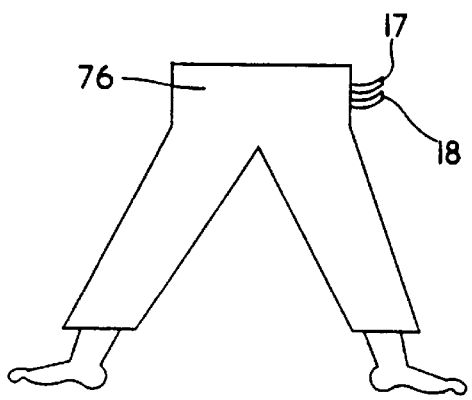
FIG. 26 is an illustration of a pants pad.

FIG. 26 shows a pants pad 76, which may be used to treat hypothermia or hyperthermia. Both the therapeutic vest and pants pad may be used with the inflating pressure device in an emergency to help immobilize a patient who needs to be transported to health care facilities.

The temperature of the therapeutic pad is controlled by the temperature control unit. The keypad referred to above and connected to the microprocessor provides the selection of a number of options and functions for the operation of the temperature control unit. The function keys include a single cycle key which allows the operator to set the unit for one temperature for a given length of time, a multicycle key which allows the operator to set the unit for at least one low temperature for a length of time and at least one high temperature for a length of time and to cycle between the low and high temperatures, a memory key which allows the operator to recall a stored cycle (either single or multi), to store new cycles, and to delete stored cycles from memory, an options key which allows the user to change the clock setting and to choose between Fahrenheit and Celsius, and which allows the operator to perform system diagnostics. There is also a preset key which allows doctors and other professionals to preset the unit for any temperature, any number of cycles, and any length of time for a patient. When the unit is preset, it will only perform the preset parameters. When finished, the preset function must be cleared in order for the unit to return to normal operations. A passcode is required to utilize the preset function.

Action keys on the keypad include start and stop keys for the timer, pump, and the coolers. When the start key is pressed again after the stop key has been pressed, the pump and coolers start, but the timer does not resume its count down until the unit again reaches the set point temperature.

The keypad also includes a number of data entry keys having various functions. An escape key allows the user to escape from one screen and go back to the preceding screen. Each depression of the key displays the previous screen. The enter key used after the numeric or up/down keys enter the selected function or parameter. The clear key allows the operator to clear a numeric field before pressing the enter key. The numeric keys allow the operator to enter numeric data, and the arrow keys allow the operator to scroll through stored cycles in the memory, to change the set point temperature during the operation of the unit such that each depression of the key(s) changes the temperature up or down by one degree, and allow for data selection by scrolling the flashing cursor through the available choices.

The keypad is connected to a liquid electronic display (LED). The power LED indicates when power is applied to the unit. The low set point LED flashes when the unit is cooling down to the set point temperature. When the set point is reached, the LED remains lit. Similarly, the high set point LED flashes when the unit is warming up to the set point temperature. When the set point is reached, the LED remains lit. The low fluid level LED lights up when fluid needs to be added to the reservoir. The function key LEDs light up when the corresponding function key is pressed, and the action key LEDS light up when the corresponding action key is pressed.

Corresponding to the LED displays the alarm system will sound when the unit is powered on, the reservoir fluid level is low (or has been refilled), a cycle(s) is completed or an error condition exists.

After switching on the temperature control unit, the sound alert "beeps" or "buzzes", fan start up occurs, all LEDs light momentarily and then extinguish except for the POWER LED, and the unit will perform a systems check which will indicate on an LCD display screen that all systems are operating or that there is a system check fail. The unit will indicate which system failed.

When the systems check has been completed the screen "asks" the operator by means of the display screen to select a function, at which point the operator selects the desired function key.

If the SINGLE CYCLE FUNCTION key is selected the SINGLE CYCLE LED lights and the screen displays the following message or something analogous:

---
SELECT SYSTEM CONTROL
1. FLUID TEMPERATURE
2. SKIN TEMPERATURE
PRESS ENTER WHEN DONE

---

The operator can utilize either the numeric keys or the UP/DOWN arrow keys to move the flashing cursor to make the desired system control selection. Upon selection, the ENTER key is to be pressed.

If the operator selects the FLUID TEMPERATURE system control, the LED displays a notice to the operator to set the fluid temperature. Underneath the notice to set the fluid temperature, a flashing temperature, such as "70° F." appears. The operator utilizes the UP/DOWN arrow keys to make one degree changes in temperature, which causes the flashing LED to cease flashing and display the next numeric value either up or down in one degree increments. The operator then presses the ENTER key. Alternatively, the numeric keys can be utilized to make direct changes without scrolling through the entire numeric field. When the desired temperature is reached, the ENTER key is pushed and the selection is complete. It should be noted that the keys can be used in combination (i.e. numeric key change is pressed to read "80" on the LED, and the UP/DOWN arrow keys are pressed until the display reads "83").

At this point, if an error has been made, the CLEAR key can be used to clear all numeric data displayed so that new values can be set, before the ENTER key is pressed. If the ENTER key has been pressed and the next screen is displayed, after the operator realizes an error has been made, the ESCAPE key will return the operator to the previous screen.

If the SKIN TEMPERATURE control system is selected, the desired temperature is selected exactly as above.

After either the FLUID TEMPERATURE or SKIN TEMPERATURE control system has been selected, the timer is to be set, usually for between 1 minute and 2 hours. After the setting of the temperature, the screen will display the following:

---
SET TIMER
H:MM
(1 MIN TO 2 HRS)
PRESS ENTER WHEN DONE

---

The flashing cursor is located under the Hour field to indicate that this is the first field to be entered. If no full hour increments are to be used, a zero is entered in this field (i.e. 0:30). The selection process is as previously described.

After pressing ENTER the screen advises the operator to plug the therapeutic pad into the unit and to press the start button when ready. If the user previously chose SKIN TEMPERATURE as the system control and has not plugged the skin sensor into the unit yet, an alarm sounds when the start key is pressed and the display screen advises the operator to plug the skin sensor into the unit and press the start button when ready.

After the probe is plugged into the control unit the START button is pressed again. Of course, the operator can escape back to the SYSTEM CONTROl screen to select FLUID TEMPERATURE instead or the operator can choose another function key. However, if SKIN TEMPERATURE was chosen, the probe has to be plugged in before the unit will start.

Once these conditions are met and the START button is pressed, the pump and the coolers are activated, the START key LED lights, the LOW SETPOINT LED or HIGH SETPOINT LED starts to flash and then remains constant once the unit reaches the setpoint, and either of the following screens will appear depending upon which type of system control was chosen:

| SET TEMP  | 45 |    | SET TEMP  | 72 |
|-----------|----|----|-----------|----|
| FLUID TEMP| 70 | or | SKIN TEMP | 94 |
| TIMER     | :20|    | TIMER     | :20|

The timer value flashes until the unit reaches the setpoint temperature and then begins to count down.

The STOP key can be used at this time. If the STOP key is pressed, the pumps, coolers and the timer stop, the START LED will extinguish and the STOP LED flashes. The screen then displays:

| PRESS START |
| TO RESUME |

The operator can either press START or select a new function. If START is pressed, the pump and the coolers will start but the timer does not resume its countdown until the unit again reaches the setpoint temperature. When the timer runs out, the pump and the coolers stop, the setpoint, start and single cycle LEDs extinguish, the sound alert sounds, and the screen returns to the select-a-function screen.

Alternatively, the MULTICYCLE function can be selected. When the MULTICYCLE function key is pressed, the MULTICYCLE LED lights and the display screen requests the operator to select either the FLUID TEMPERATURE system control or the SKIN TEMPERATURE system control. After the selection is made the ENTER key is pressed, the next screen displays:

| SET FLUID TEMP | SET SKIN TEMP |
|----------------|---------------|
| LOW 70 HIGH 70 | LOW 80 HIGH 80 |
| (45 TO 112 F.) | (72 TO 95 F.) |
| PRESS ENTER WHEN DONE | PRESS ENTER WHEN DONE |

The 70 (or 80) in the LOW field flashes to indicate that this field is to be entered first. When the LOW field had been entered, the 70 (or 80) in the HIGH field begins to flash.

After the temperature is selected, the screen displays

| SET TIMER |
| LOW H:MM HIGH H:MM |
| (1 MIN TO 2 HOURS) |
| [IS THIS ACCURATE?] |
| PRESS ENTER WHEN DONE |

The H in the low field flashes to indicate that this field is entered first.

After the timer has been set the next screen indicates to the operator to set the number of cycles. After the number of cycles have been entered the next screen informs the operator to connect the pad to the unit and to press START when ready.

When the START button is pressed the sequence of events is similar to that of the SINGLE CYCLE, and the screen displays:

| SET TEMP   | 45     | SET TEMP   | 72     |
|------------|--------|------------|--------|
| FLUID TEMP | 70     | SKIN TEMP  | 94     |
| TIMER      | :20    | TIMER      | :20    |
| CYCLE      | 1 OF 3 | CYCLE      | 1 OF 3 |

The unit will go to the low setpoint first and when the timer runs out, it will go to the high setpoint. When the high setpoint timer has finished the cycle counter increments by one and the next cycle begins. When all cycles are finished, the ending sequence of events is the same as in the SINGLE CYCLE function.

If the operator of the temperature control unit wants to recall, store or delete a cycle a MEMORY key is pressed, the MEMORY LED lights and the operator selects a RECALL, STORE or DELETE cycle. When the RECALL cycle is selected the operator then selects RECALL SINGLE CYCLE or RECALL MULTI CYCLE. As with all functions, after each cycle or selection is made, the ENTER button needs to be pressed.

When the RECALL SINGLE CYCLE is selected, the first stored cycle is displayed. The UP/DOWN arrow keys can be used to scroll through the 4 stored cycles. The selection of the cycles may be made in 2 ways. Either the ENTER key can be pressed and the cycle displayed will be selected or the number of the cycle desired can be pressed to automatically make the selection. After the selection is made, the start-up and ending procedures are the same as previously described.

The RECALL MULTI CYCLE is the same process as RECALL SINGLE CYCLE.

The temperature control unit also has a STORE cycle wherein either a single or multi cycle is stored in the memory of the microprocessor unit. After a selection has been made and entered, the screen displays STORAGE COMPLETE and the screen automatically goes back to the first screen under the OPTIONS function. If the operator is finished using the MEMORY function, ESCAPE will take the operator back to the SELECT A FUNCTION screen.

The temperature control unit also has a DELETE CYCLE which, when selected, gives a choice of deleting a SINGLE CYCLE or a MULTI CYCLE. When either choice is selected, the operator can scroll through the stored cycles and when a selection is made and ENTER is pressed, the unit indicates on the screen that the deletion is complete; the screen then automatically returns to the first screen under the MEMORY function.

The temperature control unit preferably has an OPTIONS function. When selected, the OPTIONS LED lights and the operator can select from the display screen, the CLOCK SETTINGS, TEMPERATURE READOUT, or SYSTEM DIAGNOSTICS.

The CLOCK SETTINGS readout provides the time and date, and provides the current settings. A flashing cursor appears under the first digit in the TIME field. The UP/DOWN arrow keys moves the cursor between the two fields. The numeric keys are used to change the values in these fields. If no changes are to be made, the ENTER key can be pressed to leave the clock settings as they are.

The TEMPERATURE READOUT function displays the temperature in either Fahrenheit or Celsius.

The SYSTEM DIAGNOSTICS selection allows the operator to run various system tests to detect a fault. The system diagnostics may test the LED to determine that all front panel LEDs are working, to test fuse integrity, the sound alarm system, the keypad to check the switch operation of all keys on the front panel, the supply voltage which measures the 24 volt output and any other output voltages the new circuit boards may generate, the LCD Display which displays every pixel of the display unit and the Temperature Sensor.

The temperature control unit also has a PRESET function key. This key is for prescription coding of the temperature control unit by physicians for specific clinical treatment of a patient. When the function key is pressed, the PRESET LED lights and the physician, upon request from the display screen, enters the 4 digit code. The physician then selects SINGLE CYCLE, MULTI CYCLE or CLEAR PRESET.

When the SINGLE CYCLE or MULTI CYCLE is chosen, the data entry process is the same as before except the given parameter are different. They are as follows:

| Fluid Temp | = XX to XXX | vs | 45 to 112 |
|---|---|---|---|
| Skin Temp | = XX to XXX | vs | 72 to 95 |
| Timer | = 1 min. to XX hrs | vs | 1 min to 2 hrs |
| No. of Cycles | = 1 to XX | vs | 1 to 6 |

After the operator completes the entry of the desired data in either SINGLE CYCLE or MULTI CYCLE, the number of REPEAT CYCLES through which the unit will operate is selected. Once the ENTER button is pressed, the unit only performs the preset cycles even when the unit is turned off and back on again. After the unit has completed all preset cycles, the preset function has to be cleared to return the unit to normal operations, which is accomplished by pressing the PRESET function key, entering the passcode and selecting the CLEAR PRESET option.

As noted above, the unit has a number of "fail-safe" mechanisms. Any time the unit is on and functioning, and either the internal temperature sensor or the skin sensor fails (no input from the sensor to the circuit board) the alarm system sounds, the pump and the coolers shut off and the system will display that the system failure is either due to the fluid temp sensor or the skin temperature sensor being inoperative.

Similarly, if a failure occurs (such as the fan or the pump stops working) that causes the temperature to rise above or below the given parameters, the alarm sounds, the pump and the coolers shuts off and the screen indicates that there has been a system failure and the temperature limits have been exceeded. The unit will not resume operation until the problem has been resolved.

Additionally, if the reservoir needs to be refilled, the alarm sounds, the LOW FLUID LEVEL LED lights, and the screen indicates that the reservoir needs to be refilled. After the reservoir has been refilled, the alarm again sounds, the LOW FLUID LEVEL LED extinguishes, and the unit returns to where it was before the low level occurred. If the unit was running a cycle at the time, the screen displays

PRESS START
TO RESUME

It is to be noted that there may be variations of the display screen and the machine's operations. For instance, the machine and the display may first require the setting of the time, instead of a setting of the temperature. The display screen may also display differently worded coded messages describing the same functions or requests as those described above. There may also be variations in the ranges of temperatures and time settings allowed by the temperature control unit, and the temperature control unit may have more or less electronic options and parameters than the unit described herein. Additionally, the temperature control unit can have attached a small printer connected to the microprocessor, that allows for the printed readout of any of the programmed functions including programmed cycles, clock settings, temperature readout, system diagnostics, alarm readouts, etc.

The control system may also include other options, such as an electric pulsing massage system, with pulsing units in the therapeutic body pads, positioned either on or just below the surface of the outer layer of the pads, with an electrical connection to the control unit. The strength of the electric pulses may be adjusted by pressing a PULSING function button and adjusting the parameters of the pulses just as the temperature and time parameters were adjusted, as described above. This feature is particularly useful in chiropractic offices.

While this invention has been described in terms of specific applications to various parts of the human body, the representations have been made for illustrative purposes only and other, as well as more varied uses, may be made thereof, such as in the treatment of animals in the practice of veterinary medicine.

What is claimed is:

1. A portable temperature control system comprising a temperature control unit and at least one therapeutic body pad, wherein said temperature control unit comprises:

a means for circulating a temperature control fluid through the temperature control system;

a means for cooling or heating said temperature control fluid;

a liquid heat exchanger coupled to the means for cooling to remove heat from said temperature control fluid;

an electronic programmable temperature controller for minute adjustments of the temperature of the liquid flowing through the system, programmed to automatically provide cooling and heating cycles in any desired sequence for variable periods of time;

a power supply for powering said temperature control system; a keypad for programming the cooling and heating cycles for said variable periods of time, said keypad connected to the electronic programmable temperature controller;

at least one therapeutic body pad; and means to attach said at least one therapeutic body pad to said temperature control unit.

2. The portable temperature control system according to claim 1, wherein the means for circulating the temperature control fluid is a pump.

3. The portable temperature control system according to claim 1, wherein the means for cooling or heating the temperature control fluid is at least one thermoelectric cooler consisting essentially of an arrangement of P and N-type semiconductor materials connected electrically for effecting a Peltier effect upon the circulation of current therethrough, wherein the cooler may be utilized either as a heater or cooler in accordance with the direction of current flow.

4. The portable temperature control system according to claim 1, wherein the temperature control fluid is water.

5. The portable temperature control system according to claim 1, wherein the temperature control liquid is about 60 to 90% deionized distilled water and 40 to 10% propylene glycol.

6. The portable temperature control system according to claim 1, wherein the programmable temperature controller comprises means to sense the temperature of the circulating fluid and to control the current flow through the thermoelectric cooler to automatically maintain the temperature of the circulating fluid within prescribed limits of a preset temperature programmed into the temperature controller.

7. The portable temperature control system according to claim 6, wherein the programmable temperature controller includes a microprocessor capable of controlling the temperature of the circulating fluid within ±2° F. of the preset temperature.

8. The portable temperature control system according to claim 7, wherein the microprocessor of said programmable temperature controller can be programmed to automatically provide heating and cooling cycles in any desired sequence and duration of time.

9. The portable temperature control system according to claim 7, further comprising an audio alarm system connected to the visual display to indicate restricted flow of the temperature control liquid, low levels of the temperature control fluid, malfunctions of the temperature settings when the system is powered on, when a cycle is completed or when a programming error exists.

10. The portable temperature control system according to claim 7, wherein the temperature control unit further comprises a printer connected to the microprocessor.

11. The portable temperature control system according to claim 1, wherein said power supply comprises an international front end power supply having a direct current voltage converter adaptable with an international input power supply functional on either 40 to 60 cycles and 90 to 270 volts AC input or operational on battery power.

12. The portable temperature control system according to claim 11, further comprising a brushless DC motor for operation of a fan and a pump.

13. The portable temperature control system according to claim 11, further comprising a brushed DC motor for operation of a fan and a pump.

14. The portable temperature control system according to claim 11, further comprising a dual output system wherein there is a fixed voltage output for a pump and a fan and a programmable voltage for the coolers to regulate temperature.

15. The portable temperature control system according to claim 1, further comprising multiple ports to allow for the attachment of more than one therapeutic body pad to the unit.

16. The portable temperature control system according to claim 1, wherein said temperature control unit further comprises a display screen wherein the temperature control unit communicates with and provides instructions to an operator of said unit.

17. The portable temperature control system according to claim 1, wherein said therapeutic body pad conforms to any desired portion of the anatomy, and comprises:
  a flexible structure having fluid passageways defined therein for circulating the temperature controlled liquid therethrough, said passageways configured to enable said flexible structure to conform to the desired portion of the anatomy without crimping the fluid flow;
  an outside dermal layer to be placed on a surface of a body part of the patient;
  an outside thermal layer;
  and a fluid conduit layer positioned between the outside dermal layer and the outside thermal layer, wherein said fluid passageways are positioned between the outside dermal layer and the outside thermal layer.

18. The portable temperature control system according to claim 17, wherein said outside dermal layer of said therapeutic body pad is a sterile layer removably attached to the fluid conduit layer.

19. The portable temperature control system according to claim 17, wherein a sterile layer of said therapeutic body pad may be removably attached to the outside dermal layer.

20. The portable temperature control system according to claim 1, further comprising:
  a pump system of said portable temperature control unit for applying pressure to the therapeutic body pad;
  a pressure sleeve in the therapeutic body pad, positioned on or beneath the outside thermal layer; and
  a detachable hose connecting said pump system from said portable temperature control system to said pressure sleeve of said therapeutic body pad.

21. The portable temperature control system according to claim 1, wherein said therapeutic body pad further comprises a skin temperature sensor, positioned on the outside dermal layer of the therapeutic body pad.

22. The portable temperature control system according to claim 17, wherein said therapeutic body pad further comprises a conformable gel layer filled with a conformable gel positioned next to the outside dermal layer on the inside of the therapeutic body pad, said conformable gel being selected from the group consisting of polyglycol and barium ions, polyglycol and magnesium ions, and silicon.

23. The portable temperature control system according to claim 17, wherein said therapeutic body pad has hook and loop attachment strips to secure said body pad to the appropriate body part.

24. The portable temperature control system according to claim 17, wherein said therapeutic body pad further comprises a side loading input and output to the fluid passageways and a coupling means for quickly disconnecting said input and said output from said portable temperature control system whereby said body pad may be interchanged with a second body pad without the loss of system fluids.

25. The portable temperature control system according to claim 17, wherein said therapeutic body pad is charged with temperature control fluid before said body pad is connected to said portable temperature control system.

26. The portable temperature control system according to claim 17, wherein said therapeutic body pad further comprises an air pocket positioned between said thermal layer and said fluid conduit layer to provide flexibility and good insulative qualities.

27. The portable temperature control system according to claim 17, wherein said therapeutic body pad further comprises a thin insulating material positioned between said thermal layer and said fluid conduit layer to provide flexibility and good insulative qualities.

28. The portable temperature control system according to claim 17, wherein said therapeutic body pad is shaped in the form of pants, a brassiere, a cryo-cap, a sinus face mask, a full face mask, a vest, for use in orificial treatments, for hip and shoulder treatments, or for neck treatments.

29. The portable temperature control system according to claim 17, wherein said therapeutic body pad further comprises a felt layer positioned on the outer dermal layer in contact with a body part, such that when said felt layer is wet, temperature conductivity of said body pad is improved.

30. The portable temperature control system according to claim 1, wherein said temperature control unit further comprises a temperature sensor positioned at the fluid exit of the heat exchanger to measure the temperature of the temperature control fluid.

31. A portable temperature control system comprising a temperature control unit and at least one therapeutic body pad, wherein said temperature control unit comprises:
  a means for circulating a temperature control fluid through a temperature control system;

a means for cooling or heating said temperature control fluid;

a liquid heat exchanger coupled to the means for cooling to remove heat from said temperature control fluid;

an electronic programmable temperature controller for minute adjustments of the temperature of the liquid flowing through the system such that the control system can be programmed to provide cooling and heating cycles in any desired sequence for variable periods of time, wherein the programmable temperature controller comprises a means to sense the temperature of the circulating fluid and to control the current flow through the thermoelectric cooler to maintain the temperature of the circulating fluid within prescribed limits of a preset temperature programmed into the temperature controller and a microprocessor capable of controlling the temperature of the circulating fluid within ±2° F. of the preset temperature, wherein the microprocessor of said programmable temperature controller can be programmed to automatically provide heating and cooling cycles in any desired sequence and duration of time;

a power supply for powering said temperature control system;

a keypad for programming the cooling and heating cycles for said variable periods of time, said keypad connected to the electronic programmable temperature controller;

at least one therapeutic body pad;

means to attach said at least one therapeutic body pad to said temperature control unit: and a coded prescription preset system, which allows for the presetting of a prescripted heating and cooling therapy, and which can only be utilized by the use of a prescription passcode.

32. A portable temperature control system comprising a temperature control unit and at least one therapeutic body pad, wherein said temperature control unit comprises:

a means for circulating a temperature control fluid through a temperature control system;

a means for cooling or heating said temperature control fluid;

a liquid heat exchanger coupled to the means for cooling to remove heat from said temperature control fluid;

an electronic programmable temperature controller for minute adjustments of the temperature of the liquid flowing through the system such that the control system can be programmed to provide cooling and heating cycles in any desired sequence for variable periods of time;

a power supply for powering said temperature control system;

a keypad for programming the cooling and heating cycles for said variable periods of time, said keypad connected to the electronic programmable temperature controller;

at least one therapeutic body pad;

means to attach said at least one therapeutic body pad to said temperature control unit; and an air-liquid separator in said temperature control unit for separating air from the temperature control fluid as the temperature control fluid is recirculated through the pads and the portable temperature control unit prior to the temperature control fluid entering the pump and after exiting the therapeutic pad, said air-liquid separator comprising a small reservoir for containing the temperature control fluid, a shortened tube for transporting said temperature control fluid from said body pad to said reservoir, said shortened tube emptying said temperature control fluid into said reservoir above a highest level of said liquid in said reservoir, and an exit tube extending from near the bottom of the reservoir and leading to a low pressure side of said pump.

33. The portable temperature control system according to claim 32, wherein said air-liquid separator further comprises a level sensor connected to said alarm system, whereby said alarm system is activated when the level of said temperature control fluid drops below a predetermined level in said air-liquid separator.

34. The portable temperature control system according to claim 32, further comprising a fill bottle comprising a squeeze bottle and a quick disconnect top having a male outlet, such that said fill bottle can be attached to a refill inlet of said temperature control system, said temperature control system having a female inlet and be quickly recharged without the risk of spillage.

35. A portable temperature control system comprising a temperature control unit and at least one therapeutic body pad, wherein said temperature control unit comprises:

a means for circulating a temperature control fluid through a temperature control system;

a means for cooling or heating said temperature control fluid;

a liquid heat exchanger coupled to the means for cooling to remove heat from said temperature control fluid;

an electronic programmable temperature controller for minute adjustments of the temperature of the liquid flowing through the system such that the control system can be programmed to provide cooling and heating cycles in any desired sequence for variable periods of time;

a power supply for powering said temperature control system;

a keypad for programming the cooling and heating cycles for said variable periods of time, said keypad connected to the electronic programmable temperature controller;

at least one therapeutic body pad; and means to attach said at least one therapeutic body pad to said temperature control unit, wherein said therapeutic body pad conforms to any desired portion of the anatomy of a body, and comprises:

a noncrimpable flexible structure having fluid passageways defined therein for circulating the temperature controlled liquid therethrough;

input and output couplings means to the fluid passageways, whereby a fluid may be made to flow therethrough;

an outside dermal layer to be placed on a surface of a body of the patient;

an outside thermal layer;

a fluid conduit layer positioned between the outside dermal layer and the outside thermal layer, wherein said fluid passageways are positioned between the outside thermal layer and the outside thermal layer; and an intersecting walled structure to separate input and output couplings means to prevent fluid flowing into said liquid passageways through said input coupling from flowing directly out the output borders of said body pad are wider than the passageways from the outer borders of said body pad such that the temperature control fluid is evenly distributed as it flows through said body pad.

36. A therapeutic body pad for attachment to a temperature control unit, said body pad conforming to any desired portion of the anatomy of a body, and comprising:

a noncrimpable flexible structure having fluid passageways defined therein for circulating the temperature controlled liquid therethrough;

an input and an output to the fluid passageways, whereby a fluid may be made to flow therethrough;

means for coupling said input and said output to a portable temperature control system;

an outside dermal layer to be placed on a surface of a body part of the patient;

an outside thermal layer;

a fluid conduit layer positioned between the outside dermal layer and the outside thermal layer, wherein said fluid passageways are positioned between the outside dermal layer and the outside thermal layer; and an intersecting walled structure to separate input and output couplings means to prevent fluid flowing into said liquid passageways through said input couplings, and wherein the passageways along the outer borders of said body pad are wider than the passageways away from the outer borders of said body pad such that the temperature control fluid is evenly distributed as it flows through said body pad.

* * * * *